(12) United States Patent
Akagane

(10) Patent No.: US 9,713,457 B2
(45) Date of Patent: Jul. 25, 2017

(54) ULTRASONIC PROBE

(71) Applicant: Olympus Corporation, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/325,090

(22) Filed: Jul. 7, 2014

(65) Prior Publication Data

US 2015/0011888 A1    Jan. 8, 2015

Related U.S. Application Data

(63) Continuation of application No. PCT/JP2013/078991, filed on Oct. 25, 2013.

(Continued)

(51) Int. Cl.
*A61B 17/32* (2006.01)
*A61B 8/00* (2006.01)
(Continued)

(52) U.S. Cl.
CPC .... *A61B 8/4444* (2013.01); *A61B 17/320068* (2013.01); *A61B 17/320092* (2013.01);
(Continued)

(58) Field of Classification Search
CPC .......... A61B 8/4444; A61B 17/320068; A61B 2218/002; A61B 2218/007;
(Continued)

(56) References Cited

U.S. PATENT DOCUMENTS 4,750,488 A * 6/1988 Wuchinich ....... A61B 17/22012
604/22
5,971,949 A * 10/1999 Levin ............... A61B 17/22012
604/22

(Continued)

FOREIGN PATENT DOCUMENTS

JP      A-07-299415       11/1995
JP      A-2000-041991     2/2000
(Continued)

OTHER PUBLICATIONS

Jan. 14, 2014 International Search Report issued in International Patent Application No. PCT/JP2013/078991.

(Continued)

*Primary Examiner* — Melanie Tyson
*Assistant Examiner* — Rachel S Highland
(74) *Attorney, Agent, or Firm* — Oliff PLC

(57) ABSTRACT

A groove portion depressed from an unit outer surface toward a first perpendicular direction extends over an entire length of a transmission unit in axially parallel directions, and in the transmission unit, a sectional of a first unit component perpendicular to a longitudinal axis is a first sectional shape and a sectional shape of a second unit component perpendicular to the longitudinal axis is a second sectional shape smaller in sectional area than the first sectional shape. The sectional area changing portion changes from the first sectional shape to the second sectional shape so that a gravity center position in a case where the longitudinal axis is a reference position is consistent over the entire length of the transmission unit in the axially parallel directions.

14 Claims, 20 Drawing Sheets

Related U.S. Application Data

(60) Provisional application No. 61/718,488, filed on Oct. 25, 2012.

(51) Int. Cl.
  *A61B 17/00* (2006.01)
  *A61B 18/14* (2006.01)

(52) U.S. Cl.
  CPC . *A61B 18/1445* (2013.01); *A61B 2017/00477* (2013.01); *A61B 2218/00* (2013.01); *A61B 2218/002* (2013.01); *A61B 2218/007* (2013.01); *A61B 2560/04* (2013.01)

(58) Field of Classification Search
  CPC ........ A61B 18/1445; A61B 17/320092; A61B 2560/04; A61B 2218/00; A61B 2017/00477
  See application file for complete search history.

(56) References Cited

U.S. PATENT DOCUMENTS

| | | | | |
|---|---|---|---|---|
| 5,989,208 | A * | 11/1999 | Nita | A61B 17/22 600/467 |
| 6,056,735 | A * | 5/2000 | Okada | A61B 17/320092 606/1 |
| 6,129,735 | A * | 10/2000 | Okada | A61B 17/320068 606/169 |
| 6,241,703 | B1 * | 6/2001 | Levin | A61B 17/22012 604/22 |
| 6,309,400 | B2 | 10/2001 | Beaupre | |
| 6,497,714 | B1 * | 12/2002 | Ishikawa | A61B 17/3476 606/169 |
| 6,695,781 | B2 * | 2/2004 | Rabiner | A61B 17/320068 600/439 |
| 7,300,446 | B2 | 11/2007 | Beaupre | |
| 7,503,895 | B2 * | 3/2009 | Rabiner | A61B 17/22012 600/439 |
| 7,758,600 | B2 | 7/2010 | Beaupre | |
| 8,021,381 | B2 | 9/2011 | Beaupre | |
| 8,617,194 | B2 | 12/2013 | Beaupre | |
| 2001/0027325 | A1 | 10/2001 | Beaupre | |
| 2002/0004665 | A1 | 1/2002 | Beaupre | |
| 2004/0234924 | A1 * | 11/2004 | Hickok | A61C 3/03 433/119 |
| 2006/0235305 | A1 * | 10/2006 | Cotter | A61B 17/1604 600/459 |
| 2006/0241532 | A1 * | 10/2006 | Murakami | A61B 17/320092 601/2 |
| 2007/0106158 | A1 * | 5/2007 | Madan | A61B 8/4455 600/459 |
| 2008/0051814 | A1 | 2/2008 | Beaupre | |
| 2008/0194999 | A1 * | 8/2008 | Yamaha | A61B 17/320068 601/2 |
| 2009/0216157 | A1 * | 8/2009 | Yamada | A61B 17/320092 601/2 |
| 2010/0106173 | A1 | 4/2010 | Yoshimine | |
| 2010/0121197 | A1 * | 5/2010 | Ota | A61B 17/1671 600/462 |
| 2010/0204721 | A1 * | 8/2010 | Young | A61B 17/320068 606/169 |
| 2010/0262173 | A1 | 10/2010 | Beaupre | |
| 2011/0319918 | A1 | 12/2011 | Beaupre | |
| 2013/0131705 | A1 | 5/2013 | Akagane | |

FOREIGN PATENT DOCUMENTS

| | | |
|---|---|---|
| JP | A-2005-027809 | 2/2005 |
| WO | 2004/028349 A2 | 4/2004 |
| WO | WO 2010/047395 A1 | 4/2010 |
| WO | WO 2012/118018 A1 | 9/2012 |
| WO | WO 2012/176735 A1 | 12/2012 |

OTHER PUBLICATIONS

English Translation of May 7, 2015 International Preliminary Report on Patentability issued in International Application No. PCT/JP2013/078991.

Aug. 19, 2014 Office Action issued in Japanese Application No. 2014-527094 (with translation).

May 4, 2016 Supplementary European Search Report issued in European Patent Application No. 13848451.4.

* cited by examiner

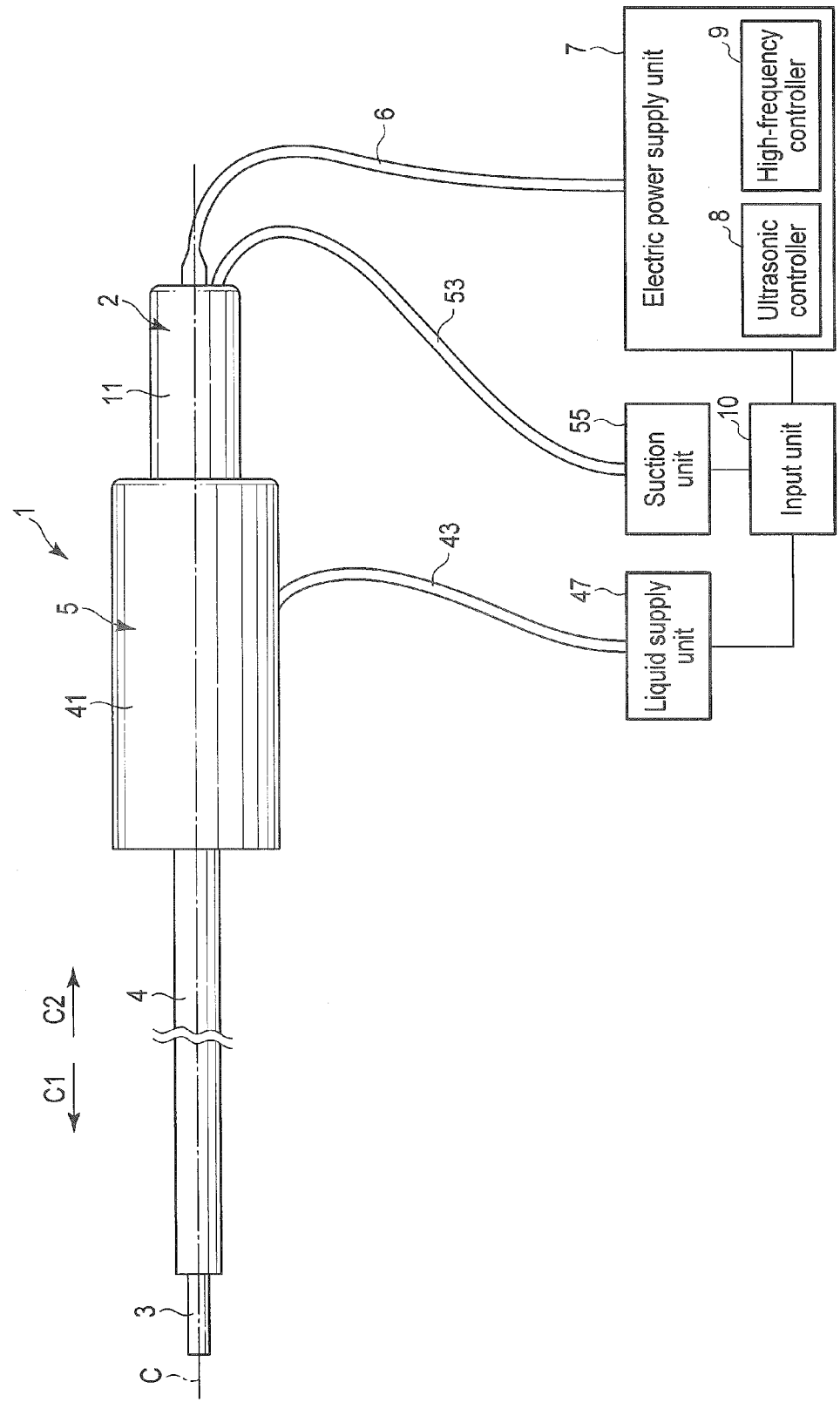
F I G. 1

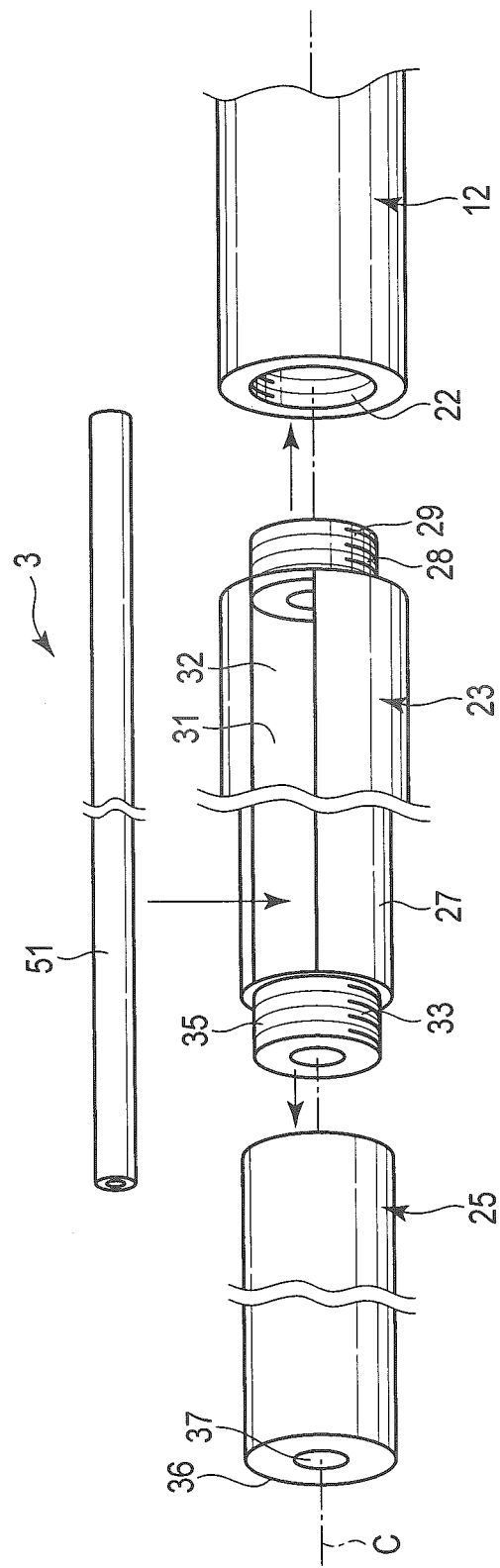
F I G. 4

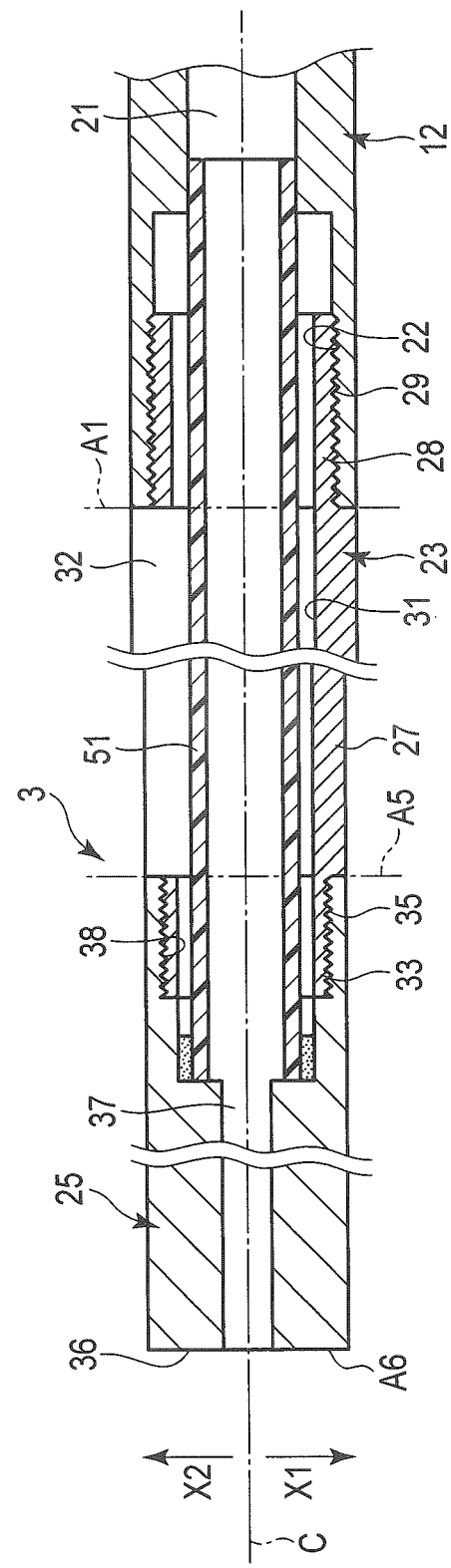
F I G. 5

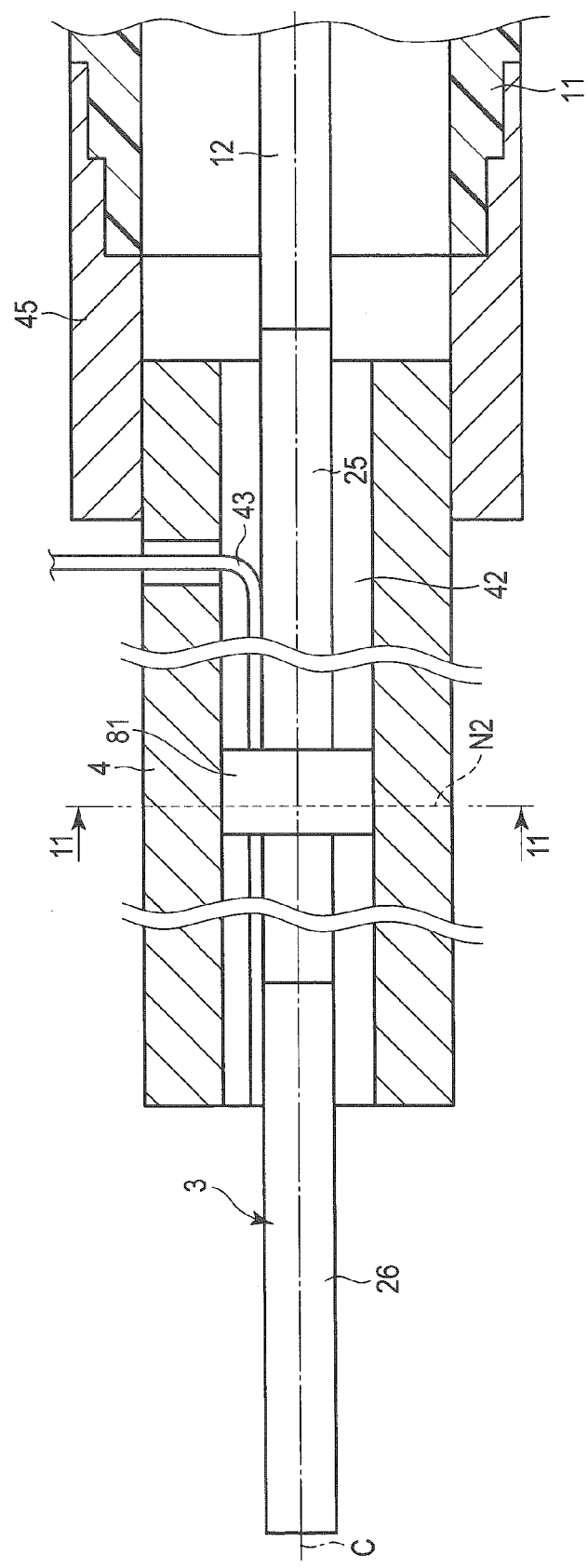
F I G. 6

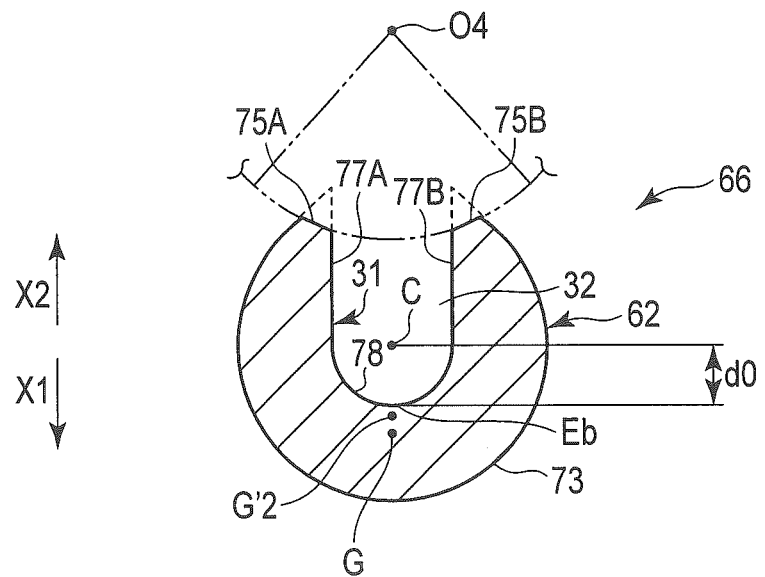
F I G. 14
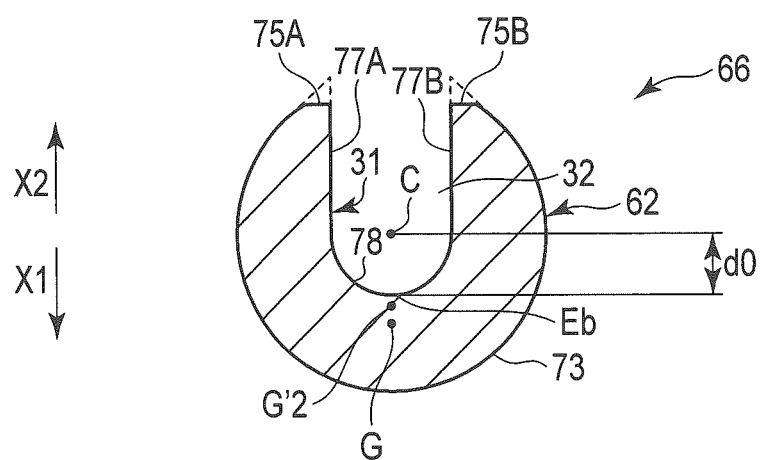
F I G. 15

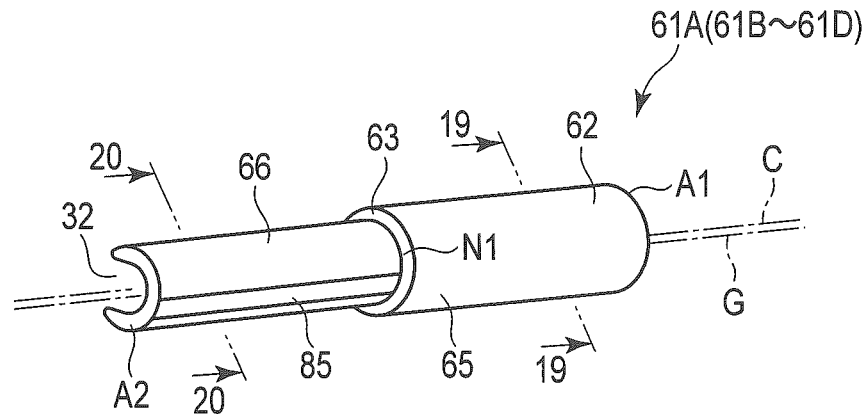
F I G. 18
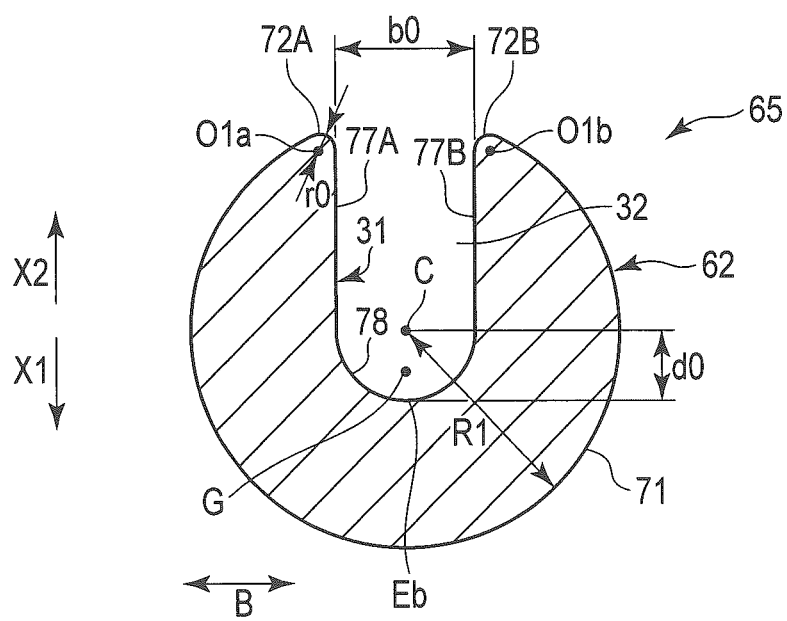
F I G. 19

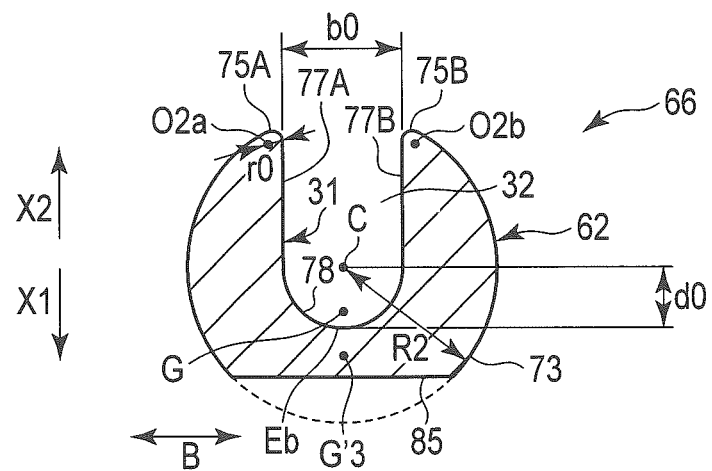
F I G. 20
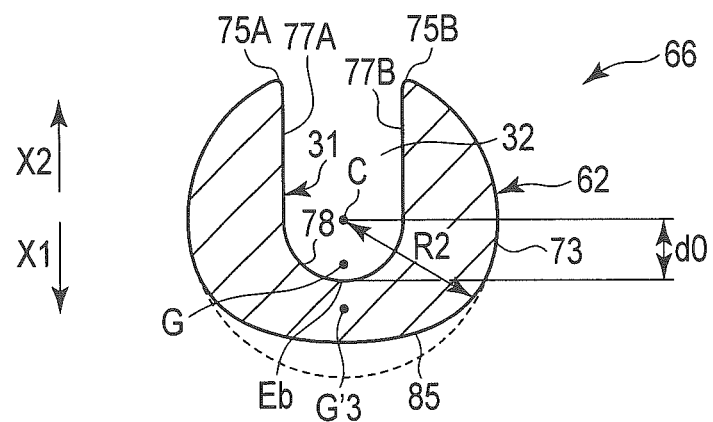
F I G. 21

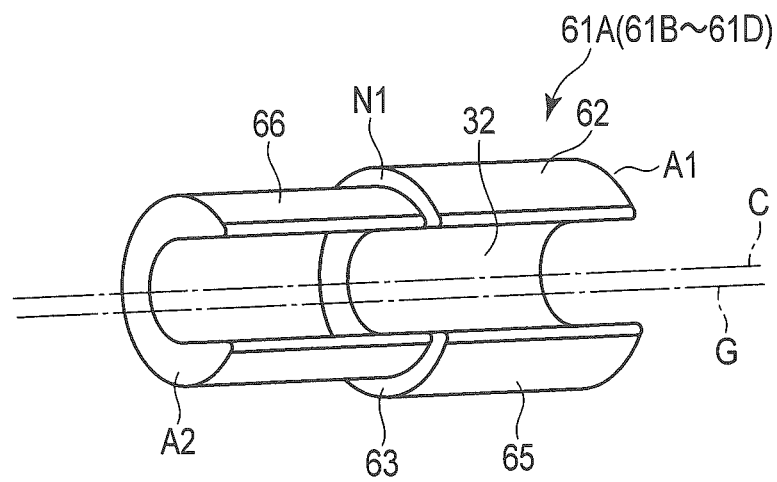
F I G. 24
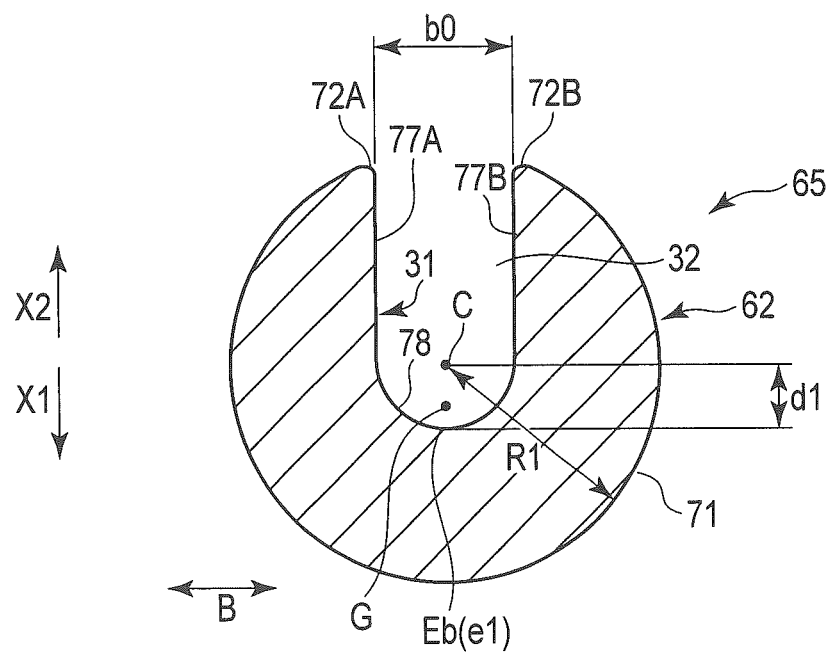
F I G. 25

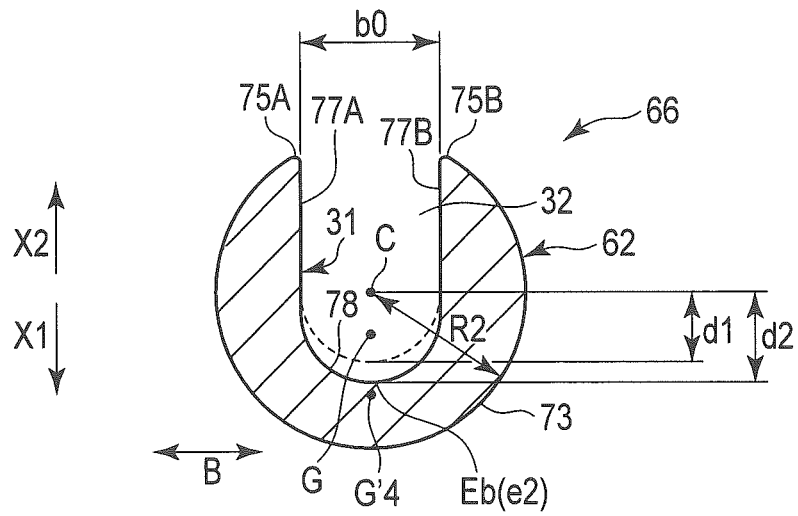
F I G. 26
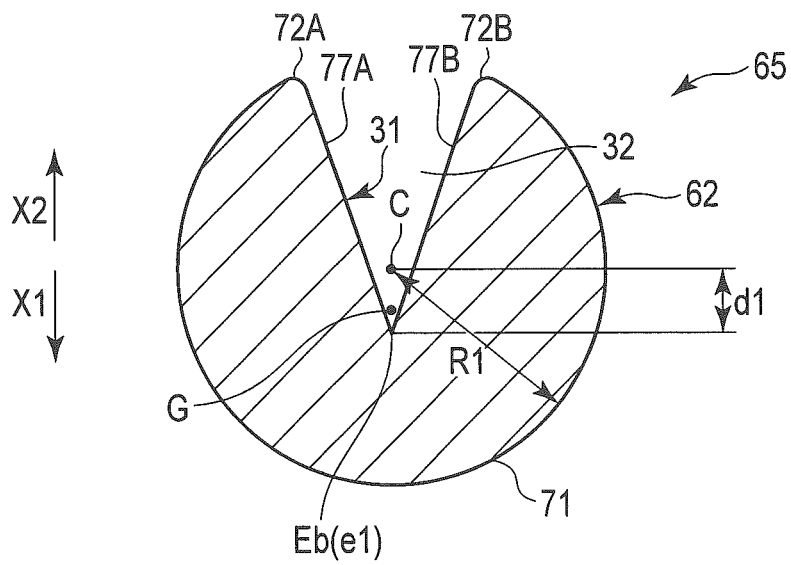
F I G. 27

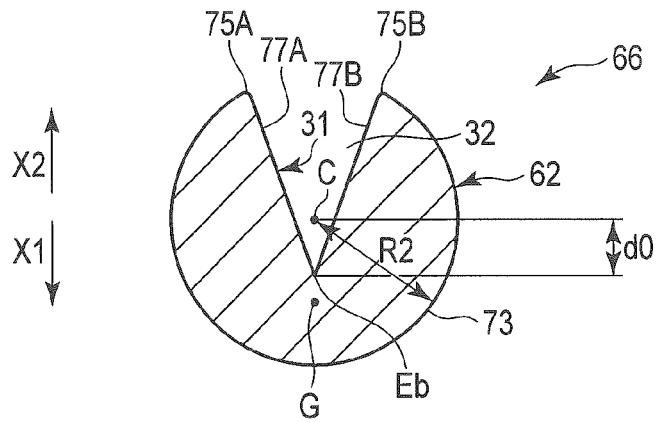
F I G. 32
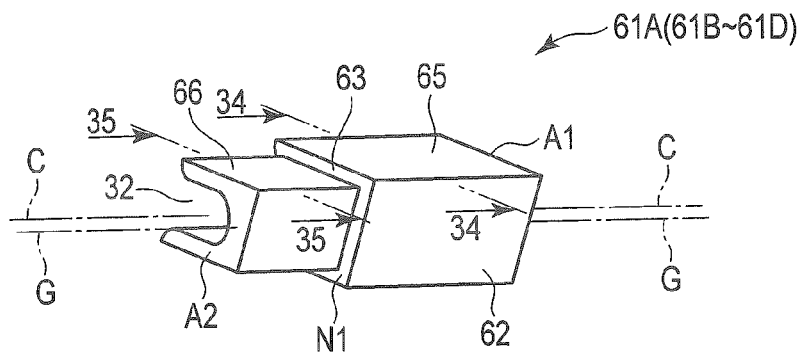
F I G. 33
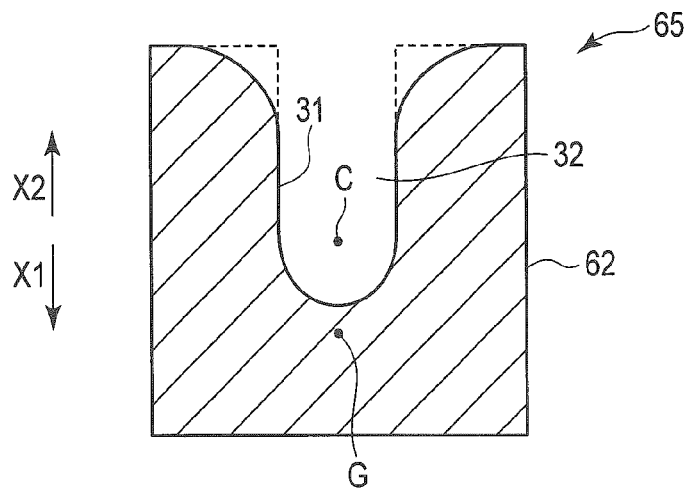
F I G. 34

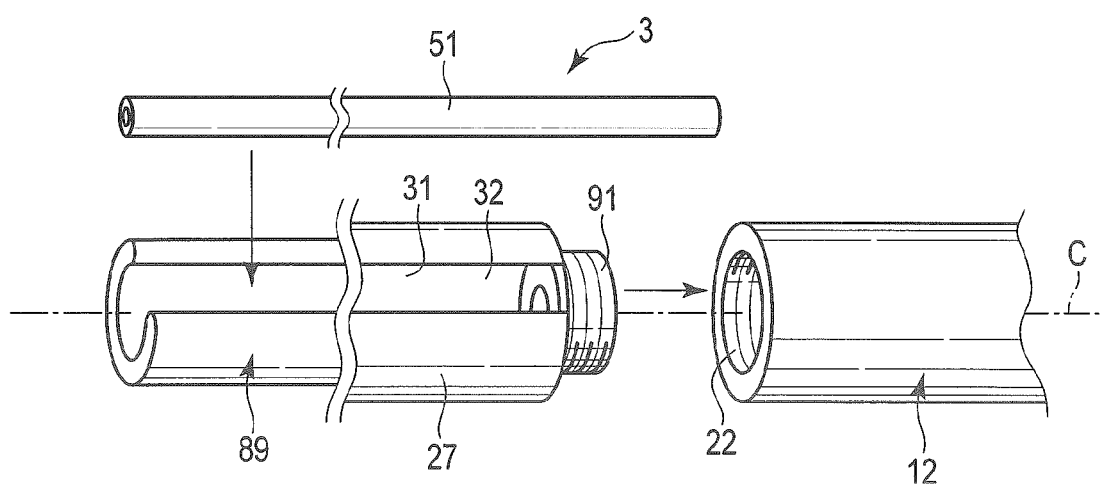
F I G. 38

ULTRASONIC PROBE

CROSS-REFERENCE TO RELATED APPLICATIONS

This is a Continuation application of PCT Application No. PCT/JP2013/078991, filed Oct. 25, 2013 and based upon and claiming the benefit of priority from prior U.S. Provisional Application No. 61/718,488, filed Oct. 25, 2012, the entire contents of which are incorporated herein by reference.

BACKGROUND OF THE INVENTION

1. Field of the Invention

The present invention relates to an ultrasonic probe used in an ultrasonic treatment device such as an ultrasonic suction device.

2. Description of the Related Art

Jpn. Pat. Appln. KOKAI Publication No. 2005-27809 has disclosed an ultrasonic treatment device to conduct an ultrasonic suction as one treatment. This ultrasonic treatment device includes an ultrasonic probe which is configured to transmit an ultrasonic vibration from a proximal direction toward a distal direction. The ultrasonic suction is conducted by using a distal face of the ultrasonically vibrating ultrasonic probe, and conducted by using a physical phenomenon known as a cavitation. More specifically, since the ultrasonic probe performs tens of thousands of high-velocity vibrations per second by an ultrasonic vibration, a pressure periodically varies in the vicinity of the distal face of the ultrasonic probe. When the pressure in the vicinity of the distal face is lower than the saturated vapor pressure for only a short time due to a pressure variation, small air bubbles (cavities) are generated in a liquid within a body cavity or in a liquid supplied from the ultrasonic treatment device to the vicinity of a treatment position of a living tissue. The generated air bubbles disappear due to a force that acts when the pressure in the vicinity of the distal face increases (compression). The above-described physical phenomenon is called a cavitation. An inelastic living tissue such as a hepatic cell is shattered and emulsified by an impact energy when the air bubbles disappear. A suction path passes through an inside of the ultrasonic probe from a proximal end to a distal end. The shattered and emulsified living tissue is suctioned and collected from a suction opening at the distal end of the ultrasonic probe through the suction path. The above-described functions are continued to resect the living tissue. In this case, an elastic living tissue such as a blood vessel absorbs the impact and is therefore not easily shattered, so that living tissues are selectively shattered. Since the suction path passes from the proximal end to the distal end (i.e., over the entire length in axially parallel directions which are parallel to a longitudinal axis) in this ultrasonic probe, the ultrasonic probe is cylindrically formed.

Jpn. PCT National Publication No. 2012/118018 has also disclosed an ultrasonic probe which is configured to transmit an ultrasonic vibration from a proximal direction toward a distal direction. This ultrasonic treatment device includes a probe body in which a groove portion is formed. The groove portion is depressed toward a first perpendicular direction perpendicular to a longitudinal axis (axially parallel directions), and is open toward a second perpendicular direction opposite to the first perpendicular direction. The groove portion is formed in the probe body in a shorter time and at lower cost than when a columnar member is perforated. Thus, the ultrasonic probe provided with the probe body in which the groove portion is formed is higher in working efficiency during manufacture and lower in manufacturing costs than the ultrasonic probe which is cylindrically formed over the entire length in the axially parallel directions.

BRIEF SUMMARY OF THE INVENTION

According to one aspect of the present invention, an ultrasonic probe which has a longitudinal axis and which is configured to transmit an ultrasonic vibration from a proximal direction toward a distal direction, the ultrasonic probe including: a transmission unit including a unit outer surface exposed to an outside, and a groove portion depressed from the unit outer surface toward a first perpendicular direction to be open toward a second perpendicular direction when two directions which are perpendicular to the longitudinal axis and which are opposite to each other are the first perpendicular direction and the second perpendicular direction, the groove portion extending over an entire length of the transmission unit in axially parallel directions parallel to the longitudinal axis, the transmission unit being point-asymmetrical with respect to the longitudinal axis; a first unit component provided in the transmission unit, the sectional shape of the first unit component perpendicular to the longitudinal axis being a first sectional shape, the first unit component having a first arc-shaped surface located a first diametrical direction dimension apart from the longitudinal axis in the first sectional shape, the first arc-shaped surface being formed on the unit outer surface; a second unit component provided to the distal direction side with respect to the first unit component in the transmission unit, the sectional shape of the second unit component perpendicular to the longitudinal axis being a second sectional shape smaller in sectional area than the first sectional shape, the second unit component having a second arc-shaped surface located a second diametrical direction dimension smaller than the first diametrical direction dimension apart from the longitudinal axis in the second sectional shape, the second arc-shaped surface being formed on the unit outer surface; and a sectional area changing portion continuous between the first unit component and the second unit component, the sectional area changing portion being located between a first antinode position which is one of antinode positions of the ultrasonic vibration and a second antinode position which is located to the distal direction side with respect to the first antinode position and which is one of the antinode positions of the ultrasonic vibration in the axially parallel directions, the sectional area changing portion changing a sectional shape perpendicular to the longitudinal axis from the first sectional shape to the second sectional shape so that a gravity center position in the case where the longitudinal axis is a reference position is consistent over the entire length of the transmission unit in the axially parallel directions, the sectional area changing portion changing the sectional area of the transmission unit perpendicular to the longitudinal axis between the first unit component and the second unit component.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing an ultrasonic treatment device according to a first embodiment of the present invention;

FIG. 4 is a perspective view schematically showing the ultrasonic probe according to the first embodiment disassembled into members;

FIG. 5 is a sectional view schematically showing the ultrasonic probe according to the first embodiment;

FIG. 6 is a sectional view schematically showing the configurations of a sheath and the ultrasonic probe according to the first embodiment;

FIG. 14 is a sectional view schematically showing the second unit component of one transmission unit according to a third modification in the section perpendicular to the longitudinal axis;

FIG. 15 is a sectional view schematically showing the second unit component of one transmission unit according to a fourth modification in the section perpendicular to the longitudinal axis;

FIG. 18 is a perspective view schematically showing the configuration of one transmission unit of a probe body according to a second embodiment;

FIG. 19 is a sectional view taken along the line 19-19 of FIG. 18;

FIG. 20 is a sectional view taken along the line 20-20 of FIG. 18;

FIG. 21 is a sectional view schematically showing the second unit component of one transmission unit according to a sixth modification in the section perpendicular to the longitudinal axis;

FIG. 24 is a perspective view schematically showing the configuration of one transmission unit of a probe body according to a third embodiment;

FIG. 25 is a sectional view schematically showing the first unit component of one transmission unit according to the third embodiment in the section perpendicular to the longitudinal axis;

FIG. 26 is a sectional view schematically showing the second unit component of one transmission unit according to the third embodiment in the section perpendicular to the longitudinal axis;

FIG. 27 is a sectional view schematically showing the first unit component of one transmission unit according to an eighth modification in the section perpendicular to the longitudinal axis;

FIG. 32 is a sectional view schematically showing the second unit component of one transmission unit according to the ninth modification in the section perpendicular to the longitudinal axis;

FIG. 33 is a perspective view schematically showing the configuration of one transmission unit of a probe body according to a tenth modification;

FIG. 34 is a sectional view taken along the line 34-34 of FIG. 33;

FIG. 38 is a perspective view schematically showing an ultrasonic probe according to a thirteenth modification disassembled into members.

DETAILED DESCRIPTION OF THE INVENTION

First Embodiment

Figure 2:
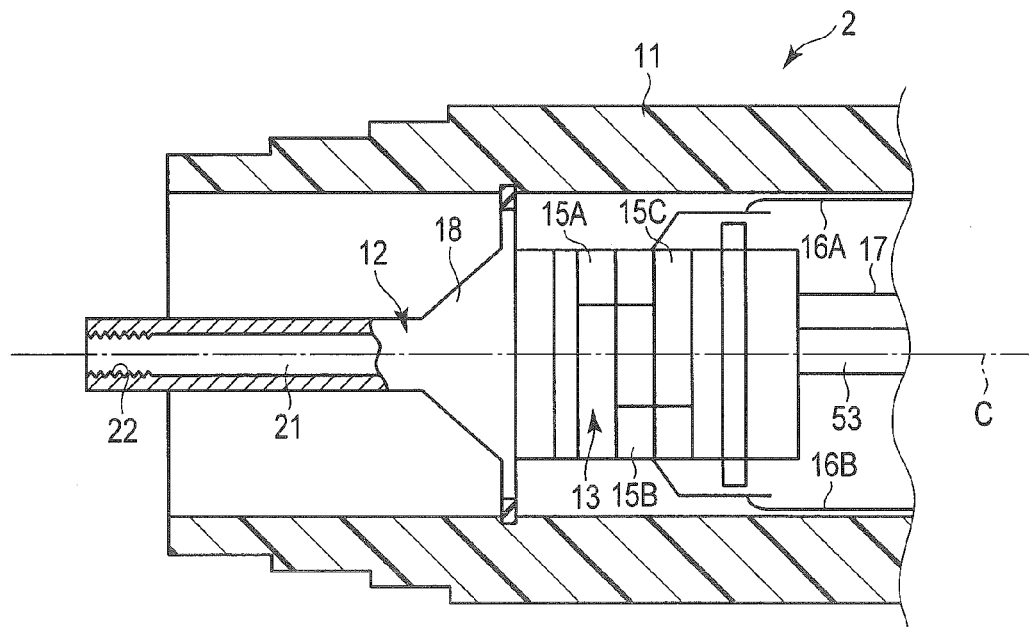
FIG. 2 is a sectional view schematically showing the configuration of a vibrator unit according to the first embodiment.

A first embodiment of the present invention is described with reference to FIG. 1 to FIG. 11. FIG. 1 is a diagram showing an ultrasonic treatment device 1 according to the present embodiment. The ultrasonic treatment device 1 according to the present embodiment is an ultrasonic suction device which selectively shatters and resects a living tissue by a cavitation caused by an ultrasonic vibration, and suctions the resected living tissue. The ultrasonic surgical device 1 also performs a treatment using a high-frequency current. Therefore, the ultrasonic treatment device 1 is an energy treatment device which uses energy such as an ultrasonic vibration and a high-frequency current to treat the living tissue which is a treatment target. The ultrasonic treatment device 1 has a longitudinal axis C. Here, one of directions parallel to the longitudinal axis C (direction of an arrow C1 in FIG. 1) is a distal direction, and the other direction parallel to the longitudinal axis C (direction of an arrow C2 in FIG. 1) is a proximal direction. The distal direction and the proximal direction are axially parallel directions parallel to the longitudinal axis C.

As shown in FIG. 1, the ultrasonic treatment device 1 includes a vibrator unit 2, an ultrasonic probe (probe unit) 3, a sheath (sheath unit) 4, and a holding unit 5. The vibrator unit 2 includes a vibrator case 11. One end of a cable 6 is connected to a proximal end of the oscillator case 11. The other end of the cable 6 is connected to an electric power supply unit 7. The electric power supply unit 7 includes an ultrasonic controller 8 and a high-frequency controller 9. An input unit 10 such as a foot switch is connected to the electric power supply unit 7.

FIG. 2 is a diagram showing the configuration of the vibrator unit 2. As shown in FIG. 2, a horn member 12 is provided inside the vibrator case 11. The horn member 12 is attached to the oscillator case 11. An ultrasonic vibrator 13 including piezoelectric elements 15A to 15C which are configured to convert an electric current to an ultrasonic vibration is attached to the horn member 12. One end of each of electric signal lines 16A and 16B is connected to the ultrasonic oscillator 13. The other end of each of the electric signal lines 16A and 16B is connected to the ultrasonic controller 8 of the electric power supply unit 7 through the cable 6. The ultrasonic vibration is generated in the ultrasonic vibrator 13 by supplying an electric current to the ultrasonic vibrator 13 from the ultrasonic controller 8 via the electric signal lines 16A and 16B. One end of an electric signal line 17 different from the electric signal lines 16A and 16B is connected to the horn member 12. The other end of the electric signal line 17 is connected to the high-frequency controller 9 of the electric power supply unit 7 through the cable 6. A high-frequency current is supplied to the horn member 12 from the high-frequency controller 9 via the electric signal line 17.

A sectional area changing portion (horn portion) 18 which is configured to increase the amplitude of the ultrasonic vibration is provided in the horn member 12. The sectional area changing portion 18 is located to the distal direction side with respect to the ultrasonic vibrator 13. A cavity portion 21 is formed in the horn member 12 about the longitudinal axis C. The cavity portion 21 extends along the longitudinal axis C from a proximal end to a distal end of the horn member 12. An internal thread portion 22 is formed at a distal portion of an inner peripheral surface of the horn member 12.

Figure 3:
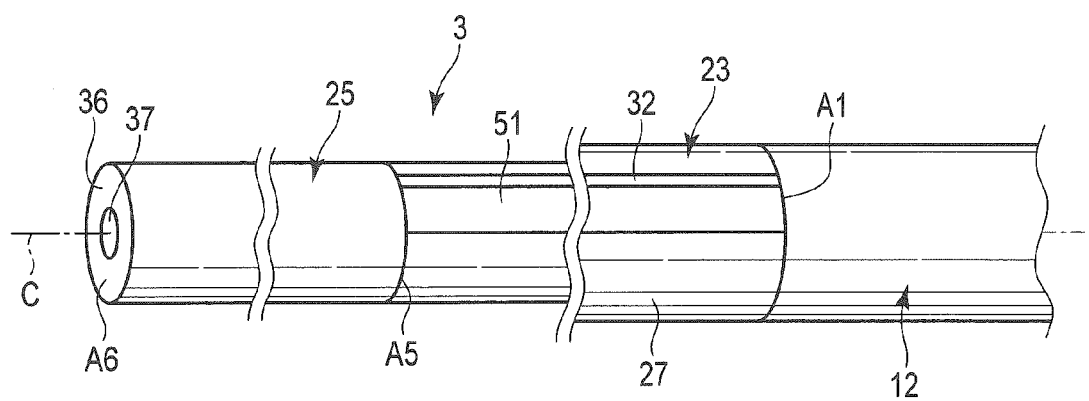
FIG. 3 is a perspective view schematically showing an ultrasonic probe according to the first embodiment.

FIG. 3 to FIG. 5 are diagrams showing the configuration of the ultrasonic probe 3. As shown in FIG. 3 to FIG. 5, the ultrasonic probe 3 includes a proximal side probe member 23 and a distal side probe member 25. The proximal side probe member 23 includes a probe body 27 extending along the longitudinal axis C.

A proximal side connection portion 28 is continuous with the proximal direction side of the probe main body 27. The proximal side connection portion 28 is cylindrically formed, and the sectional shape of the proximal side connection portion 28 perpendicular to the longitudinal axis C is point-symmetrical with respect to the longitudinal axis C. Therefore, the position of the center of gravity of the proximal side connection portion 28 is located on the longitudinal axis C in a section perpendicular to the longitudinal axis C. An external thread portion 29 is formed on an outer peripheral portion of the proximal side connection portion 28. The external thread portion 29 is screwed to the internal thread portion 22 of the horn member 12, and the proximal side probe member 23 is thereby connected to the distal direction side of the horn member 12. When the proximal side probe member 23 is connected to the horn member 12, the proximal side connection portion 28 is located inside the horn member 12 (the cavity portion 21).

As shown in FIG. 3 to FIG. 5, a groove portion 32 is defined in the probe body 27 by a groove defining portion 31 along the longitudinal axis C. The groove portion 32 extends from a proximal end to a distal end of the probe body portion 27. That is, the groove portion 32 is provided over the entire length of the probe body 27 in the axially parallel directions which are directions parallel to the longitudinal axis C. The groove portion 32 is depressed toward the first perpendicular direction (direction of an arrow X1 in FIG. 5) perpendicular to the longitudinal axis C. The groove portion 32 is open toward the second perpendicular direction (direction of an arrow X2 in FIG. 5) opposite to the first perpendicular direction.

A distal side connection portion 33 is continuous with the distal direction side of the probe main body 27. The distal side connection portion 33 is cylindrically formed, and the sectional shape of the distal side connection portion 33 perpendicular to the longitudinal axis C is point-symmetrical with respect to the longitudinal axis C. Therefore, the position of the center of gravity of the distal side connection portion 33 is located on the longitudinal axis C in the section perpendicular to the longitudinal axis C. An external thread portion 35 is formed on an outer peripheral portion of the distal side connection portion 33.

The distal side probe member 25 is cylindrically formed, and the sectional shape of the distal side probe member 25 perpendicular to the longitudinal axis C is point-symmetrical about the longitudinal axis C. A distal face 36 of the distal side probe member 25 serves as the distal end of the ultrasonic probe 3. A cavity portion 37 extends along the longitudinal axis C inside the distal side probe member 25. The cavity portion 37 is open on the distal face 36 of the distal side probe member 25 toward the distal direction. An internal thread portion 38 is provided in a proximal portion of the distal side probe member 25. The external thread portion 35 of the distal side connection portion 33 is screwed to the internal thread portion 38, and the distal side probe member 25 is thereby connected to the distal direction side of the proximal side probe member 23. When the distal side probe member 25 is connected to the proximal side probe member 23, the distal side connection portion 33 is located inside the distal side probe member 25 (the cavity portion 37).

The proximal side probe member 23 is connected to the horn member 12, and the distal side probe member 25 is connected to the proximal side probe member 23, so that the ultrasonic probe 3 is attached to the horn member 12. As a result, the ultrasonic vibration generated in the ultrasonic vibrator 13 is transmitted to the distal face 36 of the distal side probe member 25 via the horn member 12, the probe body 27 (the proximal side probe member 23), and the distal side probe member 25. That is, in the ultrasonic probe 3, the ultrasonic vibration is transmitted from the proximal direction toward the distal direction along the longitudinal axis C. The ultrasonic vibration is a longitudinal vibration having a transmission direction and a vibration direction parallel to the longitudinal axis C.

When the proximal side probe member 23 is connected to the horn member 12 and the distal side probe member 25 is connected to the proximal side probe member 23, the probe body 27 is continuous with the distal direction side of the horn member 12 at a connection antinode position A1 which is one of antinode positions of the ultrasonic vibration. Moreover, when the proximal side probe member 23 is connected to the horn member 12 and the distal side probe member 25 is connected to the proximal side probe member 23, the distal side probe member 25 is continuous with the distal direction side of the probe body 27 at a connection antinode position A5 which is located to the distal direction side with respect to the connection antinode position A1 and which is one of the antinode positions of the ultrasonic vibration. Therefore, the proximal end of the probe body 27 is located at the connection loop position A1, and the distal end of the probe body 27 is located at the connection loop position A5. Here, the groove portion 32 extends over the entire length of the probe body 27 in the axially parallel directions. Thus, the sectional shape perpendicular to the longitudinal axis C is point-asymmetrical with respect to the longitudinal axis C in the probe body 27 between the connection antinode position A1 and the connection antinode position A5.

Here, the sectional shape perpendicular to the transmission direction and the vibration direction (the longitudinal axis C) of the ultrasonic vibration changes at the connection antinode position A1. That is, the sectional shape perpendicular to the longitudinal axis C changes from the shape point-symmetrical with respect to the longitudinal axis C to the shape point-asymmetrical with respect to the longitudinal axis C at the connection antinode position A1. Similarly, the sectional shape perpendicular to the transmission direction and the vibration direction (the longitudinal axis C) of the ultrasonic vibration changes at the connection antinode position A5. That is, the sectional shape perpendicular to the longitudinal axis C changes from the shape point-asymmetrical with respect to the longitudinal axis C to the shape point-symmetrical with respect to the longitudinal axis C at the connection antinode position A5.

When the proximal side probe member 23 is connected to the horn member 12 and the distal side probe member 25 is connected to the proximal side probe member 23, the distal face 36 of the distal side probe member 25 (the distal end of the ultrasonic probe 3) is located at a most-distal antinode position A6 which is an antinode position of the ultrasonic vibration located most distally.

As shown in FIG. 1, the holding unit 5 includes a holding case 41. The ultrasonic probe 3 is inserted through the sheath 4. FIG. 6 is a diagram showing the configurations of the sheath 4 and the ultrasonic probe 3. As shown in FIG. 6, a cavity portion 42 is formed between the outer peripheral portion (outer surface) of the ultrasonic probe 3 and the inner peripheral portion of the sheath 4. A liquid supply tube 43 extends through the cavity portion 42 along the longitudinal axis C. Inside the holding case 41, the distal portion of the vibrator case 11 is attached to the proximal portion of the sheath 4 via an intermediary member 45. The liquid supply tube 43 extends from the cavity portion 42 to the outside of the sheath 4 in the proximal portion of the sheath 4.

As shown in FIG. 1, the liquid supply tube 43 extends to the outside of the holding unit 5, and is connected to a liquid supply unit 47. The liquid supply unit 47 is connected to the input unit 10. When the liquid supply unit 47 is driven, for example, by an input in the input unit 10, a liquid such as a physiological saline solution passes through an inside of the liquid supply tube 43. The liquid is then supplied to, for example, a living tissue from the distal end of the liquid supply tube 43 located between the distal end of the sheath 4 and the ultrasonic probe 3. A cavitation is caused by the transmission of the ultrasonic vibration to the distal face 36 of the distal side probe member 25 while a liquid such as a physiological saline solution is being supplied to the vicinity of the distal face 36. A living tissue having low elasticity such as a hepatic cell is selectively shattered and emulsified by the cavitation. In this case, a living tissue having high elasticity such as a blood vessel is not shattered by the cavitation. By the liquid supply to the living tissue, a bleeding part is checked, and a body cavity is, for example, washed.

As shown in FIG. 3 to FIG. 5, the ultrasonic probe 3 includes a tube member 51 extending through the groove portion 32 along the longitudinal axis C. A distal end of the tube member 51 is fixed to the inner peripheral portion of the distal side probe member 25 by, for example, adhesive bonding. The inside of the tube member 51 is in communication with the cavity portion 37 provided inside the distal side probe member 25. A proximal end of the tube member 51 is fixed to the inner peripheral portion of the horn member 12 by, for example, adhesive bonding. The inside of the tube member 51 is in communication with the cavity portion 21 provided inside the horn member 12.

As shown in FIG. 2, one end of a suction tube 53 is connected to the horn member 12. The inside of the suction tube 53 is in communication with the cavity portion 21. As shown in FIG. 1, the suction tube 53 extends to the outside of the vibrator case 11, and the other end thereof is connected to a suction unit 55. The suction unit 55 is connected to the input unit 10. When the living tissue resected by the cavitation is sucked, the suction unit 55 is driven, for example, by an input in the input unit 10. When the suction unit 55 is driven, the resected living tissue is suctioned into the cavity portion 37. The living tissue is then suctioned to the suction unit 55 through the inside of the tube member 51, the cavity portion 21, and the inside of the suction tube 53 in order.

Figure 7:
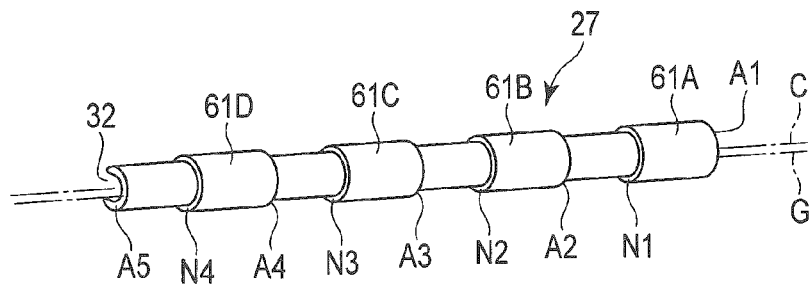
FIG. 7 is a perspective view schematically showing the configuration of a probe body of the ultrasonic probe according to the first embodiment.

FIG. 7 is a diagram showing the configuration of the probe body 27. As shown in FIG. 7, the probe body 27 includes one or more (four, in the present embodiment) transmission units 61A to 61D. The ultrasonic vibration has three antinode positions A2 to A4 between the connection antinode position A1 where the proximal end of the probe body 27 is located and the connection antinode position A5 where the distal end of the probe body 27 is located. The antinode position A3 is located to the distal direction side with respect to the antinode position A2, and the antinode position A4 is located to the distal direction side with respect to the antinode position A3. The transmission unit 61A extends from the connection antinode position A1 to the antinode position A2 along the longitudinal axis C, and the transmission unit 61B extends from the antinode position A2 to the antinode position A3 along the longitudinal axis C. The transmission unit 61C extends from the loop position A3 to the loop position A4 along the longitudinal axis C, and the transmission unit 61D extends from the antinode position A4 to the connection antinode position A5 along the longitudinal axis C.

Therefore, the distal end of the transmission unit 61A is continuous with the proximal end of the transmission unit 61B at the antinode position A2, and the distal end of the transmission unit 61B is continuous with the proximal end of the transmission unit 61C at the antinode position A3. The distal end of the transmission unit 61C is continuous with the proximal end of the transmission unit 61D at the antinode position A4. A node position N1 is located between the connection antinode position A1 and the antinode position A2, and a node position N2 is located between the antinode position A2 and the antinode position A3. A node position N3 is located between the antinode position A3 and the antinode position A4, and a node position N4 is located between the antinode position A4 and the connection antinode position A5.

Figure 8:
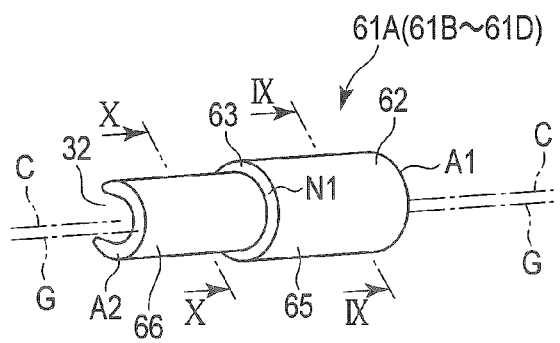
FIG. 8 is a perspective view schematically showing the configuration of one transmission unit of the probe body according to the first embodiment.
Figure 9:
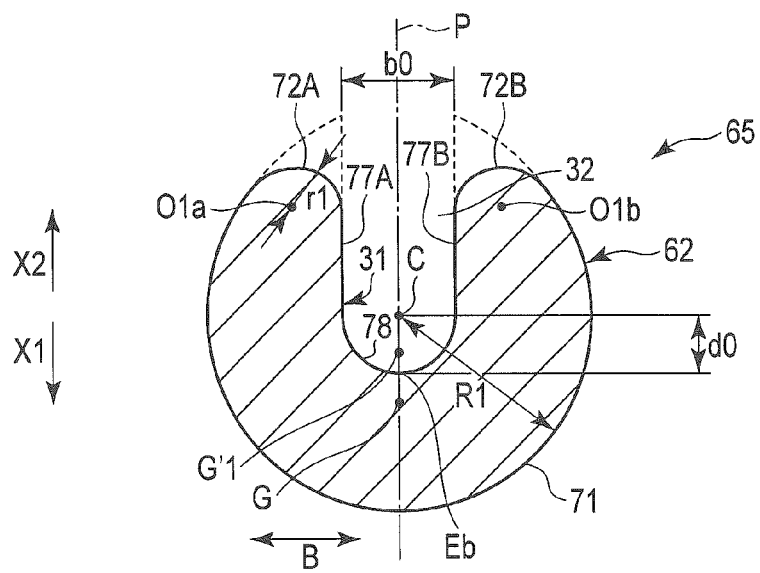
FIG. 9 is a sectional view taken along the line IX-IX of FIG. 8.
Figure 10:
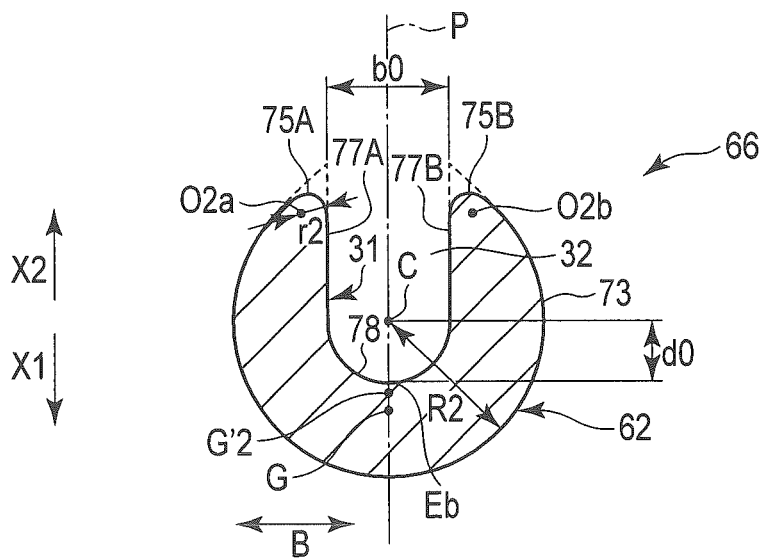
FIG. 10 is a sectional view taken along the line X-X of FIG. 8.

FIG. 8 is a diagram schematically showing the configuration of one transmission unit 61A. FIG. 9 is a sectional view taken along the line IX-IX of FIG. 8. FIG. 10 is a sectional view taken along the line X-X of FIG. 8. Although the transmission unit 61A alone is described below, the other transmission units 61B to 61D are similar to the transmission unit 61A.

As shown in FIG. 8, the transmission unit 61A includes a unit outer surface 62 serving as a part of the outer peripheral portion (outer surface) of the probe body 27. The unit outer surface 62 extends along the longitudinal axis C so that the unit outer surface 62 is exposed to the outside. As described above, in the probe body 27, the groove portion 32 is formed over the entire length in the axially parallel directions. Therefore, in the transmission unit 61A as well, the groove portion 32 is defined by the groove defining portion 31 over the entire length in the axially parallel directions. As described above, the groove portion 32 is depressed in the first perpendicular direction (direction of an arrow X1 in FIG. 9 and FIG. 10), and is open to the outside in the second perpendicular direction (direction of an arrow X2 in FIG. 9 and FIG. 10), in the section perpendicular to the longitudinal axis C. Therefore, the groove portion 32 depressed from the unit outer surface 62 toward the first perpendicular direction is formed in the transmission unit 61A.

The transmission unit 61A includes a sectional area changing portion 63 which changes the sectional area of the ultrasonic probe 3 perpendicular to the longitudinal axis C. In the present embodiment, the sectional area changing portion 63 is stepped, and is located at the node position N1 of the ultrasonic vibration in the axially parallel directions. That is, the node position N1 serves as a sectional area changing node position which changes the sectional area of the ultrasonic probe 3 perpendicular to the longitudinal axis C. The transmission unit 61A also includes a first unit component 65 extending between the connection antinode position (first antinode position) A1 and the sectional area changing portion 63 along the longitudinal axis C, and a second unit component 66 extending between the sectional area changing portion 63 and the antinode position (second antinode position) A2 along the longitudinal axis C. That is, the first unit component 65 extends between the connection antinode position (first antinode position) A1 and the node position (sectional area changing node position) N1, and the second unit component 66 extends between the node position (sectional area changing node position) N1 and the antinode position (second antinode position) A2. Therefore, FIG. 9 shows the section of the first unit component 65 perpendicular to the longitudinal axis C, and FIG. 10 shows the section of the second unit component 66 perpendicular to the longitudinal axis C.

As shown in FIG. 9, the first unit component 65 has a first sectional shape having a first sectional area S1 in the section perpendicular to the longitudinal axis C. As shown in FIG. 10, the second unit component 66 has a second sectional shape having a second sectional area S2 smaller than the first sectional area S1 in the section perpendicular to the longitudinal axis C. Therefore, the sectional area of the ultrasonic probe 3 (the probe body 27) perpendicular to the longitudinal axis C decreases in the sectional area changing portion 63. Since the sectional area of the ultrasonic probe 3 perpendicular to the longitudinal axis C decreases at the node position N1 located at a position other than the antinode positions of the ultrasonic vibration, the amplitude of the ultrasonic vibration is increased in the sectional area changing portion 63. The amplitude of the ultrasonic vibration is also increased at the node positions N2 to N4 as well as at the node position N1. As a result, the ultrasonic vibration increased in amplitude is transmitted to the distal face 36 of the ultrasonic probe 3.

At the antinode position A2 where the transmission unit 61A is continuous with the transmission unit 61B, the first unit component 65 of the transmission unit 61B is continuous with the distal direction side of the second unit component 66 of the transmission unit 61A. That is, at the antinode position A2, the sectional area of the ultrasonic probe 3 (the probe body 27) perpendicular to the longitudinal axis C increases from the second sectional area S2 to the first sectional area S1. Here, since a stress caused by the ultrasonic vibration is zero at the antinode positions of the ultrasonic vibration including the antinode position A2, the amplitude of the ultrasonic vibration does not change even if the sectional area perpendicular to a longitudinal axis has changed. Therefore, the amplitude of the ultrasonic vibration does not change at the antinode position A2 between the transmission unit 61A and the transmission unit 61B. The amplitude of the ultrasonic vibration does not change either at the antinode position A3 between the transmission unit 61B and the transmission unit 61C and at the antinode position A4 between the transmission unit 61C and the transmission unit 61D as well as at the antinode position A2.

Here, in the section perpendicular to the longitudinal axis C, the direction toward the longitudinal axis C is an inner peripheral direction, and the direction to depart from the longitudinal axis C is an outer peripheral direction. The inner peripheral direction and the outer peripheral direction are diametrical directions. As shown in FIG. 9, the first unit component 65 includes a first arc-shaped surface 71 located a first diametrical direction dimension R1 apart from the longitudinal axis C in the first sectional shape. The first arc-shaped surface 71 is a part of the unit outer surface 62, and extends in the shape of an arc around the longitudinal axis C. The first unit component 65 also includes first chamfered portions 72A and 72B continuous between the first arc-shaped surface 71 and the groove defining portion 31 in the first sectional shape. The first chamfered portions 72A and 72B are parts of the unit outer surface 62. The first arc-shaped surface 71 is continuous in directions around the longitudinal axis between the first chamfered portion 72A and the first chamfered portion 72B. Therefore, in the first sectional shape, the first arc-shaped surface 71 is continuous as the outer surface (outer peripheral portion) in a part located to the first perpendicular direction side with respect to the longitudinal axis C.

In the first sectional shape, the first chamfered portions 72A and 72B are provided so that the sectional area perpendicular to the longitudinal axis C decreases a first decrease area S'1 from a first virtual shape (shape indicated by a dotted line in FIG. 9) in which the first chamfered portions 72A and 72B are not provided. That is, the first sectional area S1 of the first sectional shape is a sectional area which has decreased by the first decrease area S'1 from the sectional area of the first virtual shape. Here, in the first virtual shape, the first arc-shaped surface 71 is directly continuous with the groove defining portion 31 (without the first chamfered portions 72A and 72B therebetween).

As shown in FIG. 10, the second unit component 66 includes a second arc-shaped surface 73 located a second diametrical direction dimension R2 smaller than the first diametrical direction dimension R1 apart from the longitudinal axis C in the second sectional shape. The second arc-shaped surface 73 is a part of the unit outer surface 62, and extends in the shape of an arc around the longitudinal axis C. The second unit component 66 also includes second chamfered portions 75A and 75B continuous between the second arc-shaped surface 73 and the groove defining portion 31 in the second sectional shape. The second chamfered portions 75A and 75B are parts of the unit outer surface 62. The second arc-shaped surface 73 is continuous in directions around the longitudinal axis between the second chamfered portion 75A and the second chamfered portion 75B. Therefore, in the second sectional shape, the second arc-shaped surface 73 is continuous as the outer surface (outer peripheral portion) in a part located to the first perpendicular direction side with respect to the longitudinal axis C.

In the second sectional shape, the second chamfered portions 75A and 75B are provided so that the sectional area perpendicular to the longitudinal axis C decreases a second decrease area S'2 from a second virtual shape (shape indicated by a dotted line in FIG. 10) in which the second chamfered portions 75A and 75B are not provided. That is, the second sectional area S2 of the second sectional shape is a sectional area which has decreased by the second decrease area S'2 from the sectional area of the second virtual shape. Here, in the second virtual shape, the second arc-shaped surface 73 is directly continuous with the groove defining portion 31 (without the second chamfered portions 75A and 75B therebetween).

As shown in FIG. 9 and FIG. 10, the groove defining portion 31 extends in a substantial U-shape in the section perpendicular to the longitudinal axis C. That is, the groove defining portion 31 includes groove side surfaces 77A and 77B (a first groove side surface 77A and a second groove side surface 77B) extending parallel to the first perpendicular direction and the second perpendicular direction in the section perpendicular to the longitudinal axis C, and a groove bottom surface 78 continuous between the groove side surface 77A and the groove side surface 77B in the section perpendicular to the longitudinal axis C. The groove bottom surface 78 is arc-shaped in the section perpendicular to the longitudinal axis C. In the transmission unit 61A (61B to 61D), the position of the groove bottom surface 78 with respect to the longitudinal axis C, that is a reference position, in the section perpendicular to the longitudinal axis C is consistent over the entire length in the axially parallel directions. Thus, in the transmission unit 61A (61B to 61D), the position of a groove bottom end Eb with respect to the longitudinal axis C served as the reference position in the first perpendicular direction and the second perpendicular direction in the section perpendicular to the longitudinal axis C is consistent over the entire length in the axially parallel directions. That is, the position of the groove bottom end Eb based on the longitudinal axis C served as the reference position does not vary between the first sectional shape of the first unit component 65 and the second sectional shape of the second unit component 66.

In the present embodiment, the groove bottom end Eb of the groove portion 32 is located to the first perpendicular direction side with respect to the longitudinal axis C over the entire length of the transmission unit 61A in the axially parallel directions. Therefore, in the present embodiment, the groove bottom end Eb of the groove portion 32 is located a predetermined bottom end dimension d0 apart from the longitudinal axis C toward the first perpendicular direction over the entire length of the transmission unit 61A in the axially parallel directions.

Here, a reference axis P which is parallel to the first perpendicular direction and the second perpendicular direction and which passes through the longitudinal axis C in the section perpendicular to the longitudinal axis C is defined. Directions which are perpendicular to the longitudinal axis C and which is perpendicular to the reference axis P (the first perpendicular direction and the second perpendicular direction) are groove width directions (directions of arrows B in FIG. 9 and FIG. 10). The dimension of the groove portion 32 in the groove width directions is a groove width dimension. In the transmission unit 61A (61B to 61D) according to the present embodiment, the groove width dimension between the groove side surface (first groove side surface) 77A and the groove side surface (second groove side surface) 77B in the section perpendicular to the longitudinal axis C is consistent over the entire length in the axially parallel directions. That is, in the transmission unit 61A (61B to 61D), the dimension between the groove side surface 77A and the groove side surface 77B in the groove width directions is a predetermined groove width dimension b0 over the entire length in the axially parallel directions. Therefore, the groove width dimension between the groove side surface 77A and the groove side surface 77B does not vary between the first sectional shape of the first unit component 65 and the second sectional shape of the second unit component 66.

Here, the first virtual shape is a shape in which the groove portion 32 having the predetermined bottom end dimension d0 and the predetermined groove width dimension b0 equal to those of the first sectional shape is formed from a first columnar shape that has a radius equal to the first diametrical direction dimension R1 and that is point-symmetrical with respect to the longitudinal axis. In the first virtual shape, the first arc-shaped surface 71 is directly continuous with the groove defining portion 31. The second virtual shape is a shape in which the groove portion 32 having the predetermined bottom end dimension d0 and the predetermined groove width dimension b0 equal to those of the second sectional shape is formed from a second columnar shape that has a radius equal to the second diametrical direction dimension R2 and that is point-symmetrical with respect to the longitudinal axis. In the second virtual shape, the second arc-shaped surface 73 is directly continuous with the groove defining portion 31. Here, the second columnar shape is a reduced shape analogous to that of the first columnar shape.

If the first virtual shape is compared with the second virtual shape, the second diametrical direction dimension R2 of the second virtual shape is smaller than the first diametrical direction dimension R1 of the first virtual shape in a diametrical direction dimension between the longitudinal axis C and the outer surface (the first arc-shaped surface 71 and the second arc-shaped surface 73). However, in the first virtual shape and the second virtual shape, the position of the groove bottom end Eb of the groove portion 32 with respect to the longitudinal axis C served as the reference position, and the groove width dimension between the groove side surface 77A and the groove side surface 77B are consistent. The first chamfered portions 72A and 72B are not provided in the first virtual shape, and the second chamfered portions 75A and 75B are not provided in the second virtual shape. Thus, a second virtual gravity center position G'2 which is a gravity center position of the second virtual shape is located to the first perpendicular direction side with respect to a first virtual gravity center position G'1 which is a gravity center position of the first virtual shape.

On the other hand, in the first sectional shape, the first chamfered portions 72A and 72B are provided, and the first arc-shaped surface 71 is continuous with the groove defining portion 31 (indirectly) via the first chamfered portions 72A and 72B. In the second sectional shape, the second chamfered portions 75A and 75B are provided, and the second arc-shaped surface 73 is continuous with the groove defining portion 31 (indirectly) via the second chamfered portions 75A and 75B. The shapes of the second chamfered portions 75A and 75B relative to the first chamfered portions 72A and 72B change between the first sectional shape and the second sectional shape. The second chamfered portions 75A and 75B change in shape relative to the first chamfered portions 72A and 72B so that a gravity center position G in the section perpendicular to the longitudinal axis C in the case where the longitudinal axis C is the reference position is consistent in the first unit component 65 and the second unit component 66.

In the present embodiment, the first chamfered portions 72A and 72B are first curved surface portions that are arc-shaped in the first sectional shape. In the first sectional shape, arc centers O1a and O1b of the first curved surface portions (72A and 72B) are located to the inner peripheral direction side with respect to the unit outer surface 62 (the first arc-shaped surface 71). The first curved surface portions (72A and 72B) have a first curvature radius r1. The second chamfered portions 75A and 75B are second curved surface portions that are arc-shaped in the second sectional shape. In the second sectional shape, arc centers O2a and O2b of the second curved surface portions (75A and 75B) are located to the inner circumferential direction side with respect to the unit outer surface 62 (the second arc-shaped surface 73). The second curved surface portions (75A and 75B) have a second curvature radius r2 smaller than the first curvature radius r1.

Here, the ratio of the first decrease area S'1 to the first sectional area S1 is a first area ratio. The ratio of the second decrease area S'2 to the second sectional area S2 is a second area ratio. In the present embodiment, the second curvature radius r2 of the second chamfered portions 75A and 75B is smaller than the first curvature radius r1 of the first chamfered portions 72A and 72B. Thus, the second area ratio is lower than the first area ratio. That is, in the region located to the second perpendicular direction side with respect to the longitudinal axis C, the area ratio (second area ratio) which is reduced by the shape change from the second virtual shape to the second sectional shape is lower than the area ratio (first area ratio) which is reduced by the shape change from the first virtual shape to the first sectional shape. Thus, the second virtual gravity center position G'2 of the second virtual shape is located to the first perpendicular direction side with respect to the first virtual gravity center position G'1 of the first virtual shape. However, between the first sectional shape and the second sectional shape, the gravity center position G in the case where the longitudinal axis C is the reference position is consistent.

As described above, between the first sectional shape and the second sectional shape, the shapes of the second chamfered portions 75A and 75B relative to the first chamfered portions 72A and 72B change so that the gravity center position G in the section perpendicular to the longitudinal axis C in the case where the longitudinal axis C is the reference position is consistent in the first unit component 65 and the second unit component 66. That is, between the first sectional shape and the second sectional shape, the shape of the unit outer surface 62 in the section perpendicular to the longitudinal axis C changes so that the gravity center position G in the section perpendicular to the longitudinal axis C in the case where the longitudinal axis C is the reference position is consistent in the first unit component 65 and the second unit component 66. Since the gravity center position G in the section perpendicular to the longitudinal axis C in the case where the longitudinal axis C is the reference position is consistent in the first unit component 65 and the second unit component 66, the gravity center position G in the section perpendicular to the longitudinal axis C in the case where the longitudinal axis C is the reference position is consistent over the entire length in the axially parallel directions in the transmission unit 61A forming a gravitational-center axis G as shown in FIGS. 8 and 9.

In each of the other transmission units 61B to 61D as well as in the transmission unit 61A, the gravity center position G in the section perpendicular to the longitudinal axis C in the case where the longitudinal axis C is the reference position is consistent over the entire length in the axially parallel directions. The gravity center position G in the section perpendicular to the longitudinal axis C in the case where the longitudinal axis C is the reference position does not vary between the transmission unit 61A and the transmission unit 61B. Between the transmission unit 61B and the transmission unit 61C and between the transmission unit 61C and the transmission unit 61D as well as between the transmission unit 61A and the transmission unit 61B, the gravity center position G in the section perpendicular to the longitudinal axis C in the case where the longitudinal axis C is the reference position does not vary. Therefore, the gravity center position G in the section perpendicular to the longitudinal axis C in the case where the longitudinal axis C is the reference position is consistent over the entire length of the probe body 27 in the axially parallel directions.

In the probe body 27 (the transmission units 61A to 61D), the gravity center position G is located on the reference axis P in the section perpendicular to the longitudinal axis C. That is, in the probe body 27, the gravity center position G is not displaced relative to the longitudinal axis C in the groove width directions. In the probe body 27, the gravity center position G is offset from the longitudinal axis C toward the first perpendicular direction.

Figure 11:
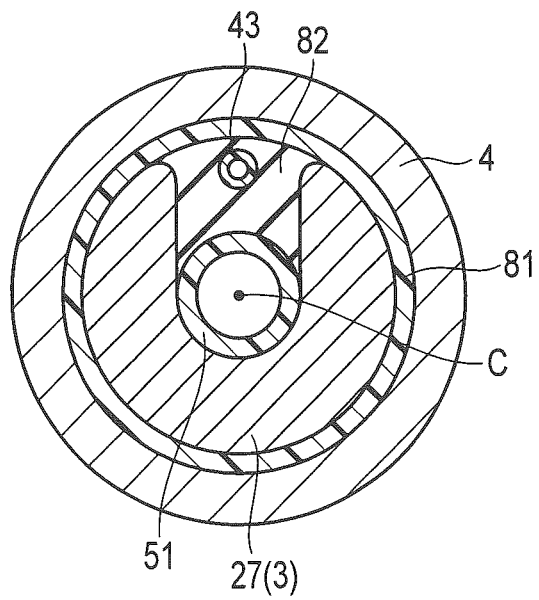
FIG. 11 is a sectional view taken along the line 11-11 of FIG. 6.

FIG. 11 is a sectional view taken along the line 11-11 of FIG. 6. As shown in FIG. 6 and FIG. 11, a cylindrical seal member 81 is provided in the cavity portion 42 between the probe body 27 of the ultrasonic probe 3 and the sheath 4. The seal member 81 is located at one of the node positions N1 to N4 of the ultrasonic vibration, and is located at the node position N2 in the present embodiment. An elastic member 82 such as rubber is provided at the node position N2. The elastic member 82 is engageable with the groove portion 32 of the probe main body 27. When the elastic member 82 is engaged with the groove portion 32 of the probe body 27, a circular cylindrical shape is formed by the probe body 27 and the elastic member 82 in the section perpendicular to the longitudinal axis C. As a result, the inner peripheral portion of the cylindrical seal member 81 comes into close contact with the outer peripheral portion (outer surface) of the probe body 27 and the outer peripheral portion of the elastic member 82. The outer peripheral portion of the seal member 81 is in close contact with the inner peripheral portion of the sheath 4. Therefore, at the node position N2, the part between the probe body 27 and the sheath 4 is kept airtight and liquidtight. As described above, the elastic member 82 is provided so that the part between the probe body 27 and the sheath 4 is also kept airtight and liquidtight at the node positions (N1 to N4) located in the probe body 27 in which the sectional shape perpendicular to the longitudinal axis C is point-asymmetrical with respect to the longitudinal axis C.

Now, the functions and advantageous effects of the ultrasonic treatment device 1 according to the present embodiment are described. When a living tissue is ultrasonically suctioned by the use of the ultrasonic treatment device 1, an electric current is supplied to the ultrasonic vibrator 13 from the ultrasonic controller 8 via the electric signal lines 16A and 16B. As a result, an ultrasonic vibration is generated in the ultrasonic vibrator 13. The generated ultrasonic vibration is transmitted to the ultrasonic probe 3 via the horn member 12. The ultrasonic vibration is then transmitted from the proximal direction toward the distal direction in the ultrasonic probe 3.

Here, at the connection antinode position A1 located at the proximal end of the probe body 27 (the distal end of the horn member 12), the sectional shape perpendicular to the longitudinal axis C changes from the shape point-symmetrical with respect to the longitudinal axis C to the shape point-asymmetrical with respect to the longitudinal axis C. At the position where the sectional shape perpendicular to the transmission direction and the vibration direction of the ultrasonic vibration greatly changes, the ultrasonic vibration is affected by the stress in directions perpendicular to the longitudinal axis C. Thus, in the present embodiment, the sectional shape perpendicular to the transmission direction and the vibration direction of the ultrasonic vibration greatly changes at the connection antinode position A1. At the loop positions of the ultrasonic vibration including the connection antinode position A1, the stress of the ultrasonic vibration is zero. Therefore, the stress does not act on the ultrasonic vibration at the connection antinode position A1 where the sectional shape perpendicular to the transmission direction and the vibration direction of the ultrasonic vibration greatly changes. Accordingly, there is no change in vibration mode.

Similarly, in the ultrasonic probe 3, the sectional shape perpendicular to the transmission direction and the vibration direction of the ultrasonic vibration greatly changes at the connection antinode position A5 located at the distal end of the probe body 27 (the proximal end of the distal side probe member 25). As described above, the stress resulting from the ultrasonic vibration is zero at the connection antinode position A5. Therefore, the stress does not act on the ultrasonic vibration at the connection antinode position A5 where the sectional shape perpendicular to the transmission direction and the vibration direction of the ultrasonic vibration greatly changes. Accordingly, there is no change in vibration mode.

As described above, the ultrasonic vibration is not affected by the stress even when a position where the sectional shape perpendicular to the longitudinal axis C changes from the shape point-symmetrical with respect to the longitudinal axis C to the shape point-asymmetrical with respect to the longitudinal axis C is provided in the ultrasonic probe 3 and the horn member 12.

The sectional area changing portion 63 is provided in each of the transmission units 61A to 61D of the probe body 27. The sectional area changing portion 63 is provided at the node position (N1 to N4) located different from the antinode position of the ultrasonic vibration, and the sectional area perpendicular to the longitudinal axis C decreases in the sectional area changing portion 63. Thus, the amplitude of the ultrasonic vibration is increased in the sectional area changing portion 63. The amplitude of the ultrasonic vibration is also increased in the probe body 27 in which the sectional shape perpendicular to the longitudinal axis C is point-asymmetrical with respect to the longitudinal axis C, so that a treatment is conducted by the use of the ultrasonic vibration increased in amplitude in the distal face 36 of the ultrasonic probe 3.

In the sectional area changing portion 63 of each of the transmission units 61A to 61D, the gravity center position G with respect the longitudinal axis C served as the reference position does not vary between the first sectional shape of the first unit component 65 and the second sectional shape of the second unit component 66. That is, in each of the transmission units 61A to 61D, the gravity center position G in the section perpendicular to the longitudinal axis C in the case where the longitudinal axis C is the reference position is consistent over the entire length in the axially parallel directions.

When the gravity center position G in the section perpendicular to the longitudinal axis C changes at positions other than the antinode positions where the stress caused by the ultrasonic vibration is zero, the ultrasonic vibration is affected by the stress. As a result, a transmissibility of the ultrasonic vibration deteriorates, and the strength of the ultrasonic probe deteriorates. Accordingly, in the present embodiment, even when the sectional area changing portion 63 is provided in each of the transmission units 61A to 61D in which the sectional shape perpendicular to the longitudinal axis C is point-asymmetrical with respect to the longitudinal axis C, the gravity center position G in the section perpendicular to the longitudinal axis C in the case where the longitudinal axis C is the reference position does not change in the sectional area changing portion 63. That is, in the probe body 27, the gravity center position G in the section perpendicular to the longitudinal axis C in the case where the longitudinal axis C is the reference position does not change at positions other than the antinode positions of the ultrasonic vibration. Therefore, the ultrasonic vibration is not affected by the stress even when the sectional area changing portion 63 is provided in each of the transmission units 61A to 61D in which the sectional shape perpendicular to the longitudinal axis C is point-asymmetrical about the longitudinal axis C.

As described above, the ultrasonic vibration is not affected by the stress in the ultrasonic probe 3 according to the present embodiment. Therefore, the transmissibility of the ultrasonic vibration is ensured, and the ultrasonic vibration is properly transmitted to the distal face 36 of the ultrasonic probe 3 (the distal side probe member 25). Since the ultrasonic vibration is not easily affected by the stress, the strength of the ultrasonic probe 3 is ensured.

The cavitation is caused by the transmission of the ultrasonic vibration to the distal face 36 of the distal side probe member 25 (the ultrasonic probe 3). A living tissue having low elasticity such as a hepatic cell is selectively shattered and resected by the cavitation. When the ultrasonic vibration is properly transmitted to the distal face 36 of the ultrasonic probe 3, the cavitation is more efficiently caused, and a treatment such as ultrasonic suction is properly conducted by the use of the cavitation.

In each of the transmission units 61A to 61D, the position of the groove bottom end Eb with respect to the longitudinal axis C served as the reference position in the first perpendicular direction and the second perpendicular direction in the section perpendicular to the longitudinal axis C is consistent over the entire length in the axially parallel directions. Thus, in each of the transmission units 61A to 61D, the groove portion 32 is easily formed by milling. The first chamfered portions 72A and 72B and the second chamfered portions 75A and 75B are also formed in a short time and at low cost. Thus, each of the transmission units 61A to 61D is efficiently formed at low cost. Therefore, the probe body 27 and the ultrasonic probe 3 can be efficiently manufactured at low cost.

The proximal side connection portion 28 which connects the probe body 27 to the horn member 12 and the distal side connection portion 33 which connects the probe body 27 to the distal side probe member 25 are cylindrically formed. That is, in the proximal side connection portion 28 and the distal side connection portion 33, the sectional shape perpendicular to the longitudinal axis C is point-symmetrical with respect to the longitudinal axis C. Thus, the strength of the proximal side connection portion and the distal side connection portion 33 is ensured even when the probe body 27 in which the sectional shape perpendicular to the longitudinal axis C is point-asymmetrical with respect to the longitudinal axis C is provided. Therefore, breakage of the proximal side connection portion 28 and the distal side connection portion 33 is effectively prevented in the connection of the probe body 27 to the horn member 12 and in the connection of the probe body 27 to the distal side probe member 25.

In the present embodiment, the part between the probe body 27 and the sheath 4 is kept airtight and liquidtight by the elastic member 82 at the node position (N2) located in the probe body 27 in which the sectional shape perpendicular to the longitudinal axis C is point-asymmetrical with respect to the longitudinal axis C. Thus, in a treatment in an abdominal cavity, pressure inside the abdominal cavity is maintained. Moreover, outflow of liquid such as body fluid from the abdominal cavity toward the proximal direction is effectively prevented in the treatment in the abdominal cavity.

Modifications of First Embodiment

Figure 12:
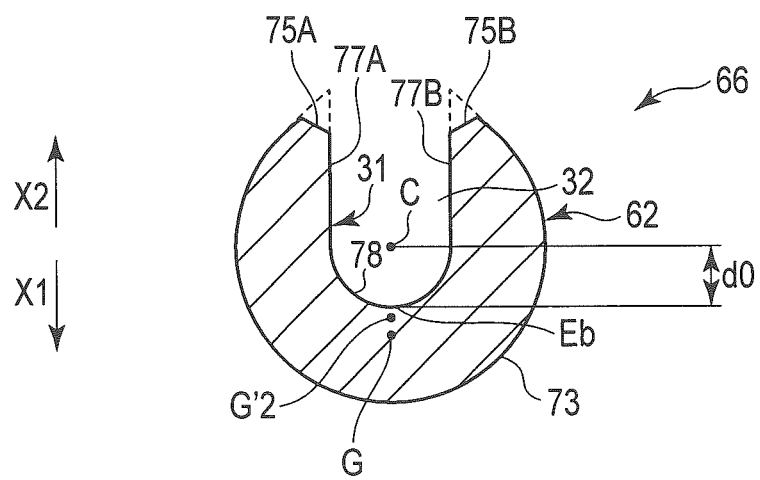
FIG. 12 is a sectional view schematically showing a second unit component of one transmission unit according to a first modification in a section perpendicular to a longitudinal axis.

The shapes of the first chamfered portions 72A and 72B and the second chamfered portions 75A and 75B are not limited to the shapes according to the first embodiment. For example, as in a first modification shown in FIG. 12, the second chamfered portions 75A and 75B may be formed into inclined planes in the second sectional shape of the second unit component 66. In the present modification, the second chamfered portions 75A and 75B extend to incline relative to the first perpendicular direction (direction of an arrow X1 in FIG. 12) and the second perpendicular direction (direction of an arrow X2 in FIG. 12).

Figure 13:
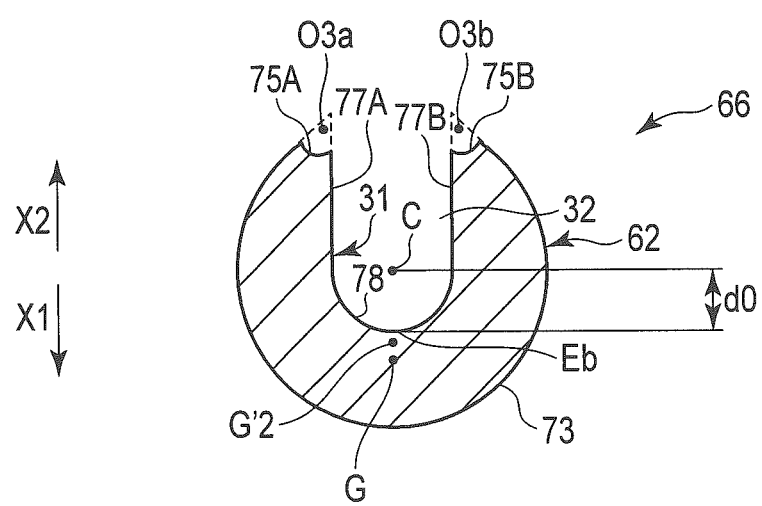
FIG. 13 is a sectional view schematically showing the second unit component of one transmission unit according to a second modification in the section perpendicular to the longitudinal axis.

For example, as in a second modification shown in FIG. 13, the second chamfered portions 75A and 75B may be formed into concave curved surfaces in the second sectional shape of the second unit component 66. In the present modification, the second chamfered portions 75A and 75B are arc-shaped so that arc centers O3a and O3b are located to the outer peripheral direction side with respect to the unit outer surface 62 (the second arc-shaped surface 73). The arc center O3a of the second chamfered portion 75A is different in position from the arc center O3b of the second chamfered portion 75B.

For example, as in a third modification shown in FIG. 14, the second chamfered portions 75A and 75B may have the same arc center O4 in the second sectional shape of the second unit component 66. In the present modification as well as in the second modification, the arc center O4 is located to the outer circumferential direction side with respect to the unit outer surface 62 (the second arc-shaped surface 73).

For example, as in a fourth modification shown in FIG. 15, the second chamfered portions 75A and 75B may be formed into planes perpendicular to the first perpendicular direction and the second perpendicular direction in the second sectional shape of the second unit component 66. In the present modification, the second chamfered portions 75A and 75B extend parallel to the groove width directions.

The first chamfered portions 72A and 72B as well as the second chamfered portions 75A and 75B may be formed into shapes such as the inclined planes or the concave curved surfaces in the first sectional shape of the first unit component 65.

In each of the transmission units 61A to 61D according to the first to fourth modifications, the second sectional area S2 of the second sectional shape of the second unit component 66 is smaller than the first sectional area S1 of the first sectional shape of the first unit component 65, as in the first embodiment. In each of the transmission units 61A to 61D, the second diametrical direction dimension R2 from the longitudinal axis C to the second arc-shaped surface 73 in the second sectional shape is smaller than the first diametrical direction dimension R1 from the longitudinal axis C to the first arc-shaped surface 71 in the first sectional shape. As in the first embodiment, in each of the transmission units 61A to 61D, the position of the groove bottom end Eb with respect to the longitudinal axis C served as the reference position in the first perpendicular direction and the second perpendicular direction in the section perpendicular to the longitudinal axis C is consistent over the entire length in the axially parallel directions. In each of the transmission units 61A to 61D, the groove width dimension between the groove side surface 77A and the groove side surface 77B in the section perpendicular to the longitudinal axis C is consistent over the entire length in the axially parallel directions.

Thus, in the first to fourth modifications, the second virtual gravity center position G'2 of the second virtual shape (shape indicated by a dotted line in FIG. 12 to FIG. 15) is located to the first perpendicular direction side with respect to the first virtual gravity center position G'1 of the first virtual shape (shape indicated by a dotted line in FIG. 9). Thus, in the first to fourth modifications as well as in the first embodiment, the second area ratio of the second decrease area S'2 to the second sectional area S2 is lower than the first area ratio of the first decrease area S'1 to the first sectional area S1. Thus, the second virtual gravity center position G'2 of the second virtual shape is located to the first perpendicular direction side with respect to the first virtual gravity center position G'1 of the first virtual shape. However, between the first sectional shape and the second sectional shape, the gravity center position G in the case where the longitudinal axis C is the reference position is consistent. That is, as in the first embodiment, between the first sectional shape and the second sectional shape, the shapes of the second chamfered portions 75A and 75B relative to the first chamfered portions 72A and 72B change so that the gravity center position G in the section perpendicular to the longitudinal axis C in the case where the longitudinal axis C is the reference position is consistent in the first unit component 65 and the second unit component 66.

Although the groove defining portion 31 extends in a substantial U-shape in the section perpendicular to the longitudinal axis C in the first embodiment, the groove defining portion 31 is not limited to this form. For example, as in a fifth modification shown in FIG. 16 and FIG. 17, the groove defining portion 31 may extend in a substantial V-shape in the section perpendicular to the longitudinal axis C. In the present modification, the groove bottom surface 78 is not provided, whereas the groove side surfaces 77A and 77B are provided. The groove side surfaces 77A and 77B extend to incline relative to the first perpendicular direction (direction of an arrow X1 in FIG. 16 and FIG. 17) and the second perpendicular direction (direction of an arrow X2 in FIG. 16 and FIG. 17).

In each of the transmission units 61A to 61D according to this modification, the second sectional area S2 of the second sectional shape of the second unit component 66 is smaller than the first sectional area S1 of the first sectional shape of the first unit component 65, as in the first embodiment. In each of the transmission units 61A to 61D, the second diametrical direction dimension R2 from the longitudinal axis C to the second arc-shaped surface 73 in the second sectional shape is smaller than the first diametrical direction dimension R1 from the longitudinal axis C to the first arc-shaped surface 71 in the first sectional shape. As in the first embodiment, in each of the transmission units 61A to 61D, the position of the groove bottom end Eb based on the longitudinal axis C served as the reference position in the first perpendicular direction and the second perpendicular direction in the section perpendicular to the longitudinal axis C is consistent over the entire length in the axially parallel directions.

Figure 16:
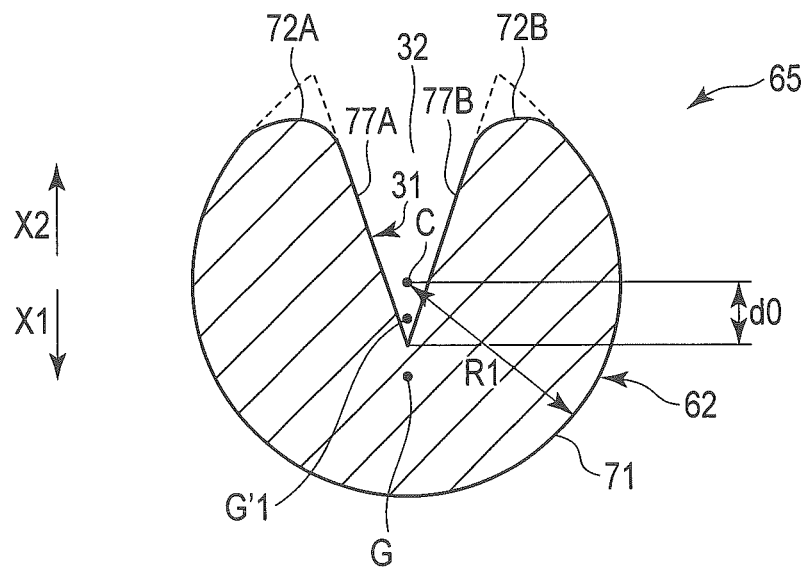
FIG. 16 is a sectional view schematically showing a first unit component of one transmission unit according to a fifth modification in the section perpendicular to the longitudinal axis.
Figure 17:
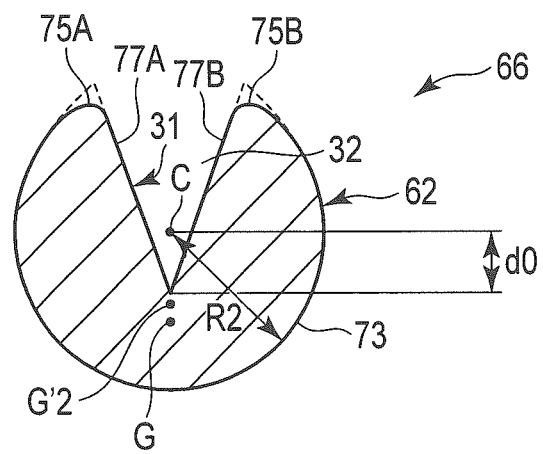
FIG. 17 is a sectional view schematically showing the second unit component of one transmission unit according to the fifth modification in the section perpendicular to the longitudinal axis.

Thus, in the present modification, the second virtual gravity center position G'2 of the second virtual shape (shape indicated by a dotted line in FIG. 17) is located to the first perpendicular direction side with respect to the first virtual gravity center position G'1 of the first virtual shape (shape indicated by a dotted line in FIG. 16). Thus, in the present modification as well as in the first embodiment, the second area ratio of the second decrease area S'2 to the second sectional area S2 is lower than the first area ratio of the first decrease area S'1 to the first sectional area S1. Thus, the second virtual gravity center position G'2 of the second virtual shape is located to the first perpendicular direction side with respect to the first virtual gravity center position G'1 of the first virtual shape. However, between the first sectional shape and the second sectional shape, the gravity center position G in the case where the longitudinal axis C is the reference position is consistent. That is, as in the first embodiment, between the first sectional shape and the second sectional shape, the shapes of the second chamfered portions 75A and 75B relative to the first chamfered portions 72A and 72B change so that the gravity center position G in the section perpendicular to the longitudinal axis C in the case where the longitudinal axis C is the reference position is consistent in the first unit component 65 and the second unit component 66.

According to the first embodiment and the first to fifth modifications described above, the unit outer surface 62 of each of the transmission units 61A to 61D has only to include the first arc-shaped surface 71 located the first diametrical direction dimension R1 apart from the longitudinal axis C in the first sectional shape, and the second arc-shaped surface 73 located the second diametrical direction dimension R2 smaller than the first diametrical direction dimension R1 apart from the longitudinal axis C in the second sectional shape. In each of the transmission units 61A to 61D, the groove portion 32 has only to be defined so that the position of the groove bottom end Eb with respect to the longitudinal axis C served as the reference position in the first perpendicular direction and the second perpendicular direction in the section perpendicular to the longitudinal axis C is consistent over the entire length in the axially parallel directions. Between the first sectional shape and the second sectional shape, the shapes of the second chamfered portions 75A and 75B relative to the first chamfered portions 72A and 72B have only to change so that the gravity center position G in the section perpendicular to the longitudinal axis C in the case where the longitudinal axis C is the reference position is consistent in the first unit component 65 and the second unit component 66.

Second Embodiment

Now, a second embodiment of the present invention is described with reference to FIG. 18 to FIG. 20. The second embodiment is a modification of the configuration according to the first embodiment, as follows. The same parts as those according to the first embodiment are indicated by the same reference signs, and are not described.

FIG. 18 is a diagram showing the configuration of one transmission unit 61A. FIG. 19 is a sectional view taken along the line 19-19 of FIG. 18. FIG. 20 is a sectional view taken along the line 20-20 of FIG. 18. Although the transmission unit 61A alone is described below, the other transmission units 61B to 61D are similar to the transmission unit 61A. FIG. 19 shows the section of the first unit component 65 perpendicular to the longitudinal axis C, and FIG. 20 shows the section of the second unit component 66 perpendicular to the longitudinal axis C.

As shown in FIG. 18 and FIG. 20, in the present embodiment as well, the second sectional area S2 of the second sectional shape of the second unit component 66 is smaller than the first sectional area S1 of the first sectional shape of the first unit component 65. Therefore, the sectional area of the ultrasonic probe 3 (the probe body 27) perpendicular to the longitudinal axis C decreases in the sectional area changing portion 63. Since the sectional area of the ultrasonic probe 3 perpendicular to the longitudinal axis C decreases at the node position N1 located at a position other than the antinode positions of the ultrasonic vibration, the amplitude of the ultrasonic vibration is increased in the sectional area changing portion 63. As a result, in the present embodiment as well, the ultrasonic vibration increased in amplitude is transmitted to the distal face 36 of the ultrasonic probe 3.

As shown in FIG. 19, the first unit component 65 includes the first arc-shaped surface 71 located the first diametrical direction dimension R1 apart from the longitudinal axis C in the first sectional shape. The first unit component 65 also includes the first chamfered portions 72A and 72B continuous between the first arc-shaped surface 71 and the groove defining portion 31 in the first sectional shape. The first arc-shaped surface 71 is continuous in the directions around the longitudinal axis between the first chamfered portion 72A and the first chamfered portion 72B. Therefore, in the first sectional shape, the first arc-shaped surface 71 is continuous as the outer surface (outer peripheral portion) in a part to the first perpendicular direction side with respect to the longitudinal axis C.

As shown in FIG. 20, the second unit component 66 includes the second arc-shaped surface 73 located the second diametrical direction dimension R2 smaller than the first diametrical direction dimension R1 apart from the longitudinal axis C in the second sectional shape. The second unit component 66 includes the second chamfered portions 75A and 75B continuous between the second arc-shaped surface 73 and the groove defining portion 31 in the second sectional shape. In the present embodiment, in contrast with the first embodiment, the second unit component 66 includes a decreasing dimension surface 85 in which a diametrical direction dimension from the longitudinal axis C is smaller than the second diametrical direction dimension R2. The decreasing dimension surface 85 is a part of the unit outer surface 62, and is provided to the first perpendicular direction side with respect to the gravity center position G in the second sectional shape. In the present embodiment, the decreasing dimension surface 85 is formed into a plane in the second sectional shape. The decreasing dimension surface 85 is provided so that in the present embodiment, the second arc-shaped surface 73 is not continuous in the directions around the longitudinal axis between the second chamfered portion 75A and the second chamfered portion 75B. That is, in the second sectional shape, the second arc-shaped surface 73 is not continuous as the outer surface (outer peripheral portion) in the part to the first perpendicular direction side with respect to the longitudinal axis C.

In the second sectional shape, the decreasing dimension surface 85 is provided so that the sectional area perpendicular to the longitudinal axis C decreases by a decrease area S'3 from a virtual shape (shape indicated by a dotted line in FIG. 20) in which the decreasing dimension surface 85 is not provided. That is, the second sectional area S2 of the second sectional shape is a sectional area which has decreased by the decrease area S'3 from the sectional area of the virtual shape. Here, in the virtual shape, the second arc-shaped surface 73 is continuous in the directions around the longitudinal axis between the second chamfered portion 75A and the second chamfered portion 75B.

The groove defining portion 31 extends in a substantial U-shape in the section perpendicular to the longitudinal axis C. In the transmission unit 61A (61B to 61D), as in the first embodiment, the position of the groove bottom surface 78 with respect to the longitudinal axis C served as the reference position in the section perpendicular to the longitudinal axis C is consistent over the entire length in the axially parallel directions. Thus, in the transmission unit 61A (61B to 61D), the position of a groove bottom end Eb based on the longitudinal axis C served as the reference position in the first perpendicular direction and the second perpendicular direction in the section perpendicular to the longitudinal axis C is consistent over the entire length in the axially parallel directions. That is, the position of the groove bottom end Eb with respect to the longitudinal axis C served as the reference position does not vary between the first sectional shape of the first unit component 65 and the second sectional shape of the second unit component 66.

In the transmission unit 61A (61B to 61D) according to the present embodiment, the groove width dimension between the groove side surface (first groove side surface) 77A and the groove side surface (second groove side surface) 77B in the section perpendicular to the longitudinal axis C is consistent over the entire length in the axially parallel directions. That is, in the transmission unit 61A (61B to 61D), the dimension between the groove side surface 77A and the groove side surface 77B in the groove width directions is the predetermined groove width dimension b0 over the entire length in the axially parallel directions. Therefore, the groove width dimension between the groove side surface 77A and the groove side surface 77B does not vary between the first sectional shape of the first unit component 65 and the second sectional shape of the second unit component 66.

The first chamfered portions 72A and 72B according to the present embodiment are the first curved surface portions that are arc-shaped in the first sectional shape. In the first sectional shape, the arc centers O1a and O1b of the first curved surface portions (72A and 72B) are located to the inner peripheral direction side with respect to the unit outer surface 62 (the first arc-shaped surface 71). The second chamfered portions 75A and 75B are the second curved surface portions that are arc-shaped in the second sectional shape. In the second sectional shape, the arc centers O2a and O2b of the second curved surface portions (75A and 75B) are located to the inner peripheral direction side with respect to the unit outer surface 62 (the second arc-shaped surface 73). The first curved surface portions (72A and 72B) and the second curved surface portions (75A and 75B) have the same curvature radius r0. Therefore, in the present embodiment, in contrast with the first embodiment, the shapes of the second chamfered portions 75A and 75B do not change relative to the first chamfered portions 72A and 72B between the first sectional shape and the second sectional shape.

Here, the first sectional shape is a shape in which the groove portion 32 having the predetermined bottom end dimension d0 and the predetermined groove width dimension b0 is formed in the first columnar shape that has a radius equal to the first diametrical direction dimension R1 and that is point-symmetrical with respect to the longitudinal axis. In the first sectional shape, the first chamfered portions 72A and 72B are formed. The virtual shape and the second sectional shape are shapes in which the groove portion 32 having the predetermined bottom end dimension d0 and the predetermined groove width dimension b0 is formed from the second columnar shape that has a radius equal to the second diametrical direction dimension R2 and that is point-symmetrical about the longitudinal axis. In the virtual shape and the second virtual shape, the second chamfered portions 75A and 75B having the same curvature radius r0 as the first chamfered portions 72A and 72B are formed. Here, the second columnar shape is a reduced shape analogous to that of the first columnar shape.

If the first sectional shape is compared with the virtual shape, the second diametrical direction dimension R2 of the virtual shape is smaller than the first diametrical direction dimension R1 of the first sectional shape in a diametrical direction dimension between the longitudinal axis C and the outer surface (the first arc-shaped surface 71 and the second arc-shaped surface 73). However, in the first sectional shape and the virtual shape, the position of the groove bottom end Eb of the groove portion 32 with respect to the longitudinal axis C served as the reference position, and the groove width dimension between the groove side surface 77A and the groove side surface 77B are consistent. The shapes of the first chamfered portions 72A and 72B of the first sectional shape and the second chamfered portions 75A and 75B of the virtual shape are substantially correspond with each other in the section perpendicular to the longitudinal axis C. The first arc-shaped surface 71 is continuous between the first chamfered portion 72A and the first chamfered portion 72B in the first sectional shape, and the second arc-shaped surface 73 is continuous between the second chamfered portion 75A and the second chamfered portion 75B in the virtual shape. Thus, a virtual gravity center position G'3, which is the gravity center position of the virtual shape, is located to the first perpendicular direction side with respect to the gravity center position G of the first sectional shape.

On the other hand, in the second sectional shape, the decreasing dimension surface 85 is provided to the first perpendicular direction side with respect to the gravity center position G. Thus, in the second sectional shape, the second arc-shaped surface 73 is not continuous between the second chamfered portion 75A and the second chamfered portion 75B. Between the first sectional shape and the second sectional shape, the shape of the decreasing dimension surface 85 relative to the first arc-shaped surface 71 changes in a part to the first perpendicular direction side with respect to the gravity center position G. The decreasing dimension surface 85 changes in shape relative to the first arc-shaped surface 71 so that the gravity center position G in the section perpendicular to the longitudinal axis C in the case where the longitudinal axis C is the reference position is consistent in the first unit component 65 and the second unit component 66.

In the second sectional shape, the decreasing dimension surface 85 is provided so that the sectional area is the second sectional area S2 which has decreased by the decrease area S'3 from the sectional area of the virtual shape. That is, in the region to the first perpendicular direction side with respect to the longitudinal axis C, the sectional area is reduced by the shape change from the virtual shape to the second sectional shape. Thus, the virtual gravity center position G'3 of the virtual shape is located to the first perpendicular direction side with respect to the gravity center position G of the first sectional shape. However, between the first sectional shape and the second sectional shape, the gravity center position G in the case where the longitudinal axis C is the reference position is consistent.

As described above, between the first sectional shape and the second sectional shape, the shape of the decreasing dimension surface 85 relative to the first arc-shaped surface 71 changes so that the gravity center position G in the section perpendicular to the longitudinal axis C in the case where the longitudinal axis C is the reference position is consistent in the first unit component 65 and the second unit component 66. That is, between the first sectional shape and the second sectional shape, the shape of the unit outer surface 62 in the section perpendicular to the longitudinal axis C changes so that the gravity center position G in the section perpendicular to the longitudinal axis C in the case where the longitudinal axis C is the reference position is consistent in the first unit component 65 and the second unit component 66. Since the gravity center position G in the section perpendicular to the longitudinal axis C in the case where the longitudinal axis C is the reference position is consistent in the first unit component 65 and the second unit component 66, the gravity center position G in the section perpendicular to the longitudinal axis C in the case where the longitudinal axis C is the reference position is consistent over the entire length in the axially parallel directions in the transmission unit 61A.

In each of the other transmission units 61B to 61D as well as in the transmission unit 61A, the gravity center position G in the section perpendicular to the longitudinal axis C in the case where the longitudinal axis C is the reference position is consistent over the entire length in the axially parallel directions. The gravity center position G in the section perpendicular to the longitudinal axis C in the case where the longitudinal axis C is the reference position does not vary between the transmission unit 61A and the transmission unit 61B. Between the transmission unit 61B and the transmission unit 61C and between the transmission unit 61C and the transmission unit 61D as well as between the transmission unit 61A and the transmission unit 61B, the gravity center position G in the section perpendicular to the longitudinal axis C in the case where the longitudinal axis C is the reference position does not change. Therefore, the gravity center position G in the section perpendicular to the longitudinal axis C in the case where the longitudinal axis C is the reference position is consistent over the entire length of the probe body 27 in the axially parallel directions.

In the sectional area changing portion 63 of each of the transmission units 61A to 61D in the ultrasonic probe 3 according to the present embodiment, the gravity center position G with respect to the longitudinal axis C served as the reference position does not vary between the first sectional shape of the first unit component 65 and the second sectional shape of the second unit component 66, as in the first embodiment. That is, in each of the transmission units 61A to 61D, the gravity center position G in the section perpendicular to the longitudinal axis C in the case where the longitudinal axis C is the reference position is consistent over the entire length in the axially parallel directions. Accordingly, even when the sectional area changing portion 63 is provided in each of the transmission units 61A to 61D in which the sectional shape perpendicular to the longitudinal axis C is point-asymmetrical with respect to the longitudinal axis C, the gravity center position G in the section perpendicular to the longitudinal axis C in the case where the longitudinal axis C is the reference position does not change in the sectional area changing portion 63. That is, in the probe body 27, the gravity center position G in the section perpendicular to the longitudinal axis C in the case where the longitudinal axis C is the reference position does not change at positions other than the antinode positions of the ultrasonic vibration. Therefore, the ultrasonic vibration is not affected by the stress even when the sectional area changing portion 63 is provided in each of the transmission units 61A to 61D in which the sectional shape perpendicular to the longitudinal axis C is point-asymmetrical with respect to the longitudinal axis C.

As in the first embodiment, the ultrasonic vibration is not affected by the stress in the ultrasonic probe 3 according to the present embodiment. Therefore, a transmissibility of the ultrasonic vibration is ensured, and the ultrasonic vibration is properly transmitted to the distal face 36 of the ultrasonic probe 3 (the distal side probe member 25). As in the first embodiment, the ultrasonic vibration is not easily affected by the stress, so that the strength of the ultrasonic probe 3 is ensured.

In each of the transmission units 61A to 61D, the position of the groove bottom end Eb with respect to the longitudinal axis C served as the reference position in the first perpendicular direction and the second perpendicular direction in the section perpendicular to the longitudinal axis C is consistent over the entire length in the axially parallel directions. Thus, in each of the transmission units 61A to 61D, the groove portion 32 is easily formed by milling. The decreasing dimension surface 85 is also formed in a short time and at low cost. Thus, each of the transmission units 61A to 61D is efficiently formed at low cost. Therefore, the probe body 27 and the ultrasonic probe 3 can be efficiently manufactured at low cost as in the first embodiment.

Modifications of Second Embodiment

Although the decreasing decrease surface 85 is formed into a plane in the second sectional shape in the second embodiment, the decreasing dimension surface 85 is not limited to this shape. For example, as in a sixth modification shown in FIG. 21, the decreasing dimension surface 85 may be formed into a curved surface in the second sectional shape. However, in the present modification as well as in the second embodiment, the decreasing dimension surface 85 of the second unit component 66 is provided to the first perpendicular direction side with respect to the gravity center position G in the second sectional shape. The diametrical direction dimension from the longitudinal axis C to the decreasing dimension surface 85 is smaller than the second diametrical direction dimension R2.

In each of the transmission units 61A to 61D according to the present modification, the second sectional area S2 of the second sectional shape of the second unit component 66 is smaller than the first sectional area S1 of the first sectional shape of the first unit component 65, as in the second embodiment. In each of the transmission units 61A to 61D, the second diametrical direction dimension R2 from the longitudinal axis C to the second arc-shaped surface 73 in the second sectional shape is smaller than the first diametrical direction dimension R1 from the longitudinal axis C to the first arc-shaped surface 71 in the first sectional shape. As in the second embodiment, in each of the transmission units 61A to 61D, the position of the groove bottom end Eb with respect to the longitudinal axis C served as the reference position in the first perpendicular direction and the second perpendicular direction in the section perpendicular to the longitudinal axis C is consistent over the entire length in the axially parallel directions. In each of the transmission units 61A to 61D, the groove width dimension between the groove side surface 77A and the groove side surface 77B in the section perpendicular to the longitudinal axis C is consistent over the entire length in the axially parallel directions. The shapes of the second chamfered portions 75A and 75B do not change relative to the first chamfered portions 72A and 72B between the first sectional shape and the second sectional shape.

Thus, in the present modification, the virtual gravity center position G'3 of the virtual shape (shape indicated by a dotted line in FIG. 21) is located to the first perpendicular direction side with respect to the gravity center position G of the first sectional shape. Accordingly, in the second sectional shape according to the present modification, the decreasing dimension surface 85 is provided so that the sectional area perpendicular to the longitudinal axis C decreases by the decrease area S'3 from the virtual shape, as in the second embodiment. Thus, the virtual gravity center position G'3 of the virtual shape is located to the first perpendicular direction side with respect to the gravity center position G of the first sectional shape. However, between the first sectional shape and the second sectional shape, the gravity center position G in the case where the longitudinal axis C is the reference position is consistent. That is, as in the second embodiment, the shape of the decreasing dimension surface 85 relative to the first arc-shaped surface 71 changes between the first sectional shape and the second sectional shape so that the gravity center position G in the section perpendicular to the longitudinal axis C in the case where the longitudinal axis C is the reference position is consistent in the first unit component 65 and the second unit component 66.

Figure 22:
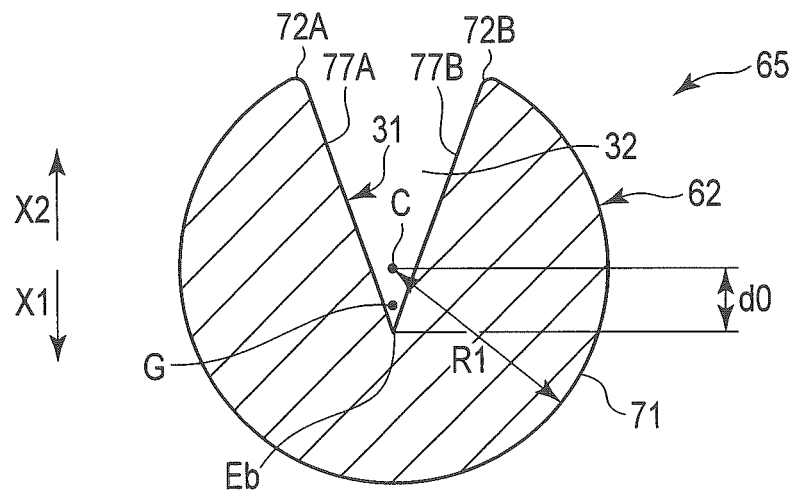
FIG. 22 is a sectional view schematically showing the first unit component of one transmission unit according to a seventh modification in the section perpendicular to the longitudinal axis.
Figure 23:
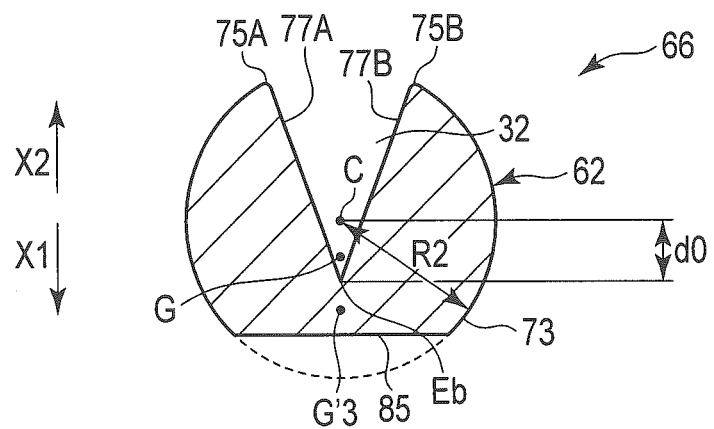
FIG. 23 is a sectional view schematically showing the second unit component of one transmission unit according to the seventh modification in the section perpendicular to the longitudinal axis.

Although the groove defining portion 31 extends in a substantial U-shape in the section perpendicular to the longitudinal axis C in the second embodiment, the groove defining portion 31 is not limited to this form. For example, as in a seventh modification shown in FIG. 22 and FIG. 23, the groove defining portion 31 may extend in a substantial V-shape in the section perpendicular to the longitudinal axis C. In the present modification, the groove bottom surface 78 is not provided, whereas the groove side surfaces 77A and 77B are provided. The groove side surfaces 77A and 77B extend to incline relative to the first perpendicular direction (direction of an arrow X1 in FIG. 22 and FIG. 23) and the second perpendicular direction (direction of an arrow X2 in FIG. 22 and FIG. 23).

In each of the transmission units 61A to 61D according to the present modification as well, the second sectional area S2 of the second sectional shape of the second unit component 66 is smaller than the first sectional area S1 of the first sectional shape of the first unit component 65, as in the second embodiment. In each of the transmission units 61A to 61D, the second diametrical direction dimension R2 from the longitudinal axis C to the second arc-shaped surface 73 in the second sectional shape is smaller than the first diametrical direction dimension R1 from the longitudinal axis C to the first arc-shaped surface 71 in the first sectional shape. As in the second embodiment, in each of the transmission units 61A to 61D, the position of the groove bottom end Eb based on the longitudinal axis C served as the reference position in the first perpendicular direction and the second perpendicular direction in the section perpendicular to the longitudinal axis C is consistent over the entire length in the axially parallel directions.

Thus, in the present modification, the virtual gravity center position G'3 of the virtual shape (shape indicated by a dotted line in FIG. 23) is located to the first perpendicular direction side with respect to the gravity center position G of the first sectional shape. Accordingly, in the second sectional shape according to the present modification, the decreasing dimension surface 85 is provided so that the sectional area perpendicular to the longitudinal axis C decreases by the decrease area S'3 from the virtual shape, as in the second embodiment. Thus, the virtual gravity center position G'3 of the virtual shape is located to the first perpendicular direction side with respect to the gravity center position G of the first sectional shape. However, between the first sectional shape and the second sectional shape, the gravity center position G in the case where the longitudinal axis C is the reference position is consistent. That is, as in the second embodiment, the shape of the decreasing dimension surface 85 relative to the first arc-shaped surface 71 changes between the first sectional shape and the second sectional shape so that the gravity center position G in the section perpendicular to the longitudinal axis C in the case where the longitudinal axis C is the reference position is consistent in the first unit component 65 and the second unit component 66.

According to the second embodiment and the sixth and seventh modifications described above, the unit outer surface 62 of each of the transmission units 61A to 61D has only to include the first arc-shaped surface 71 located the first diametrical direction dimension R1 apart from the longitudinal axis C in the first sectional shape, and the second arc-shaped surface 73 located the second diametrical direction dimension R2 smaller than the first diametrical direction dimension R1 apart from the longitudinal axis C in the second sectional shape. In each of the transmission units 61A to 61D, the groove portion 32 has only to be defined so that the position of the groove bottom end Eb with respect to the longitudinal axis C served as the reference position in the first perpendicular direction and the second perpendicular direction in the section perpendicular to the longitudinal axis C is consistent over the entire length in the axially parallel directions. Between the first sectional shape and the second sectional shape, the shape of the decreasing dimension surface 85 relative to the first arc-shaped surface 71 has only to change so that the gravity center position in the section perpendicular to the longitudinal axis C in the case where the longitudinal axis C is the reference position is consistent in the first unit component 65 and the second unit component 66.

Configuration Associated with First Embodiment and Second Embodiment

In the first embodiment, the shapes of the second chamfered portions 75A and 75B relative to the first chamfered portions 72A and 72B change between the first sectional shape and the second sectional shape. In the second embodiment, the shape of the decreasing dimension surface 85 relative to the first arc-shaped surface 71 changes between the first sectional shape and the second sectional shape. In the first embodiment, the first chamfered portions 72A and 72B and the second chamfered portions 75A and 75B are parts of the unit outer surface 62. In the second embodiment, the first arc-shaped surface 71 and the decreasing dimension surface 85 are parts of the unit outer surface 62.

Therefore, in the ultrasonic probe 3 having the configuration associated with the first embodiment and the second embodiment (the first to seventh modifications are included), the unit outer surface 62 of each of the transmission units 61A to 61D includes the first arc-shaped surface 71 located the first diametrical direction dimension R1 apart from the longitudinal axis C in the first sectional shape, and the second arc-shaped surface 73 located the second diametrical direction dimension R2 smaller than the first diametrical direction dimension R1 apart from the longitudinal axis C in the second sectional shape. In each of the transmission units 61A to 61D, the groove portion 32 is defined so that the position of the groove bottom end Eb with respect to the longitudinal axis C served as the reference position in the first perpendicular direction and the second perpendicular direction in the section perpendicular to the longitudinal axis C is consistent over the entire length in the axially parallel directions. Between the first sectional shape and the second sectional shape, the shape of the unit outer surface 62 in the section perpendicular to the longitudinal axis C changes so that the gravity center position G in the section perpendicular to the longitudinal axis C in the case where the longitudinal axis C is the reference position is consistent in the first unit component 65 and the second unit component 66.

Third Embodiment

Now, a third embodiment of the present invention is described with reference to FIG. 24 to FIG. 26. The third embodiment is the following modification of the configurations according to the first embodiment and the second embodiment. The same parts as those according to the first embodiment and the second embodiment are indicated by the same reference signs, and are not described.

FIG. 24 is a diagram showing the configuration of one transmission unit 61A. FIG. 25 is a sectional view of the first unit component 65 perpendicular to the longitudinal axis C, and FIG. 26 is a sectional view of the second unit component 66 perpendicular to the longitudinal axis C. Although the transmission unit 61A alone is described below, the other transmission units 61B to 61D are similar to the transmission unit 61A.

As shown in FIG. 24 to FIG. 26, in the present embodiment as well, the second sectional area S2 of the second sectional shape of the second unit component 66 is smaller than the first sectional area S1 of the first sectional shape of the first unit component 65. Therefore, the sectional area of the ultrasonic probe 3 (the probe body 27) perpendicular to the longitudinal axis C decreases in the sectional area changing portion 63. Since the sectional area of the ultrasonic probe 3 perpendicular to the longitudinal axis C decreases at the node position N1 located at a position other than the antinode positions of the ultrasonic vibration, the amplitude of the ultrasonic vibration is increased in the sectional area changing portion 63. As a result, in the present embodiment as well, the ultrasonic vibration increased in amplitude is transmitted to the distal face 36 of the ultrasonic probe 3.

As shown in FIG. 25, the first unit component 65 includes the first arc-shaped surface 71 located the first diametrical direction dimension R1 apart from the longitudinal axis C in the first sectional shape. The first unit component 65 also includes the first chamfered portions 72A and 72B continuous between the first arc-shaped surface 71 and the groove defining portion 31 in the first sectional shape. The first arc-shaped surface 71 is continuous in the directions around the longitudinal axis between the first chamfered portion 72A and the first chamfered portion 72B. Therefore, in the first sectional shape, the first arc-shaped surface 71 is continuous as the outer surface in a part to the first perpendicular direction side with respect to the longitudinal axis C.

As shown in FIG. 26, the second unit component 66 includes the second arc-shaped surface 73 located the second diametrical direction dimension R2 smaller than the first diametrical direction dimension R1 apart from the longitudinal axis C in the second sectional shape. The second unit component 66 includes the second chamfered portions 75A and 75B continuous between the second arc-shaped surface 73 and the groove defining portion 31 in the second sectional shape. The second arc-shaped surface 73 is continuous in the directions around the longitudinal axis between the second chamfered portion 75A and the second chamfered portion 75B. Therefore, in the second sectional shape, the second arc-shaped surface 73 is continuous as the outer surface in a part to the first perpendicular direction side with respect to the longitudinal axis C. In the present embodiment as well as in the second embodiment, the shapes of the second chamfered portions 75A and 75B do not change relative to the first chamfered portions 72A and 72B between the first sectional shape and the second sectional shape.

The groove defining portion 31 extends in a substantial U-shape in the section perpendicular to the longitudinal axis C. In the transmission unit 61A (61B to 61D), the groove width dimension between the groove side surface (first groove side surface) 77A and the groove side surface (second groove side surface) 77B in the section perpendicular to the longitudinal axis C is consistent over the entire length in the axially parallel directions. That is, in the transmission unit 61A (61B to 61D), the dimension between the groove side surface 77A and the groove side surface 77B in the groove width directions is the predetermined groove width dimension b0 over the entire length in the axially parallel directions. Therefore, the groove width dimension between the groove side surface 77A and the groove side surface 77B does not vary between the first sectional shape of the first unit component 65 and the second sectional shape of the second unit component 66.

However, in the transmission unit 61A (61B to 61D) according to the present embodiment, in contrast with the first embodiment and the second embodiment, the position of the groove bottom surface 78 with respect to the longitudinal axis C served as the reference position in the section perpendicular to the longitudinal axis C differs between the first sectional shape and the second sectional shape. Thus, in the transmission unit 61A (61B to 61D), the position of the groove bottom end Eb based on the longitudinal axis C served as the reference position in the first perpendicular direction and the second perpendicular direction in the section perpendicular to the longitudinal axis C changes between the first sectional shape and the second sectional shape. In the first sectional shape, the groove bottom end Eb is located at a first bottom end position e1. In the second sectional shape, the groove bottom end Eb is located at a second bottom end position e2 located to the first perpendicular direction side with respect to the first bottom end position e1. The first bottom end position e1 and the second bottom end position e2 are located to the first perpendicular direction side with respect to the longitudinal axis C.

In the second sectional shape, the groove bottom end Eb is located at the second bottom end position e2 so that the sectional area perpendicular to the longitudinal axis C decreases by a decrease area S'4 from the virtual shape (shape indicated by a dotted line in FIG. 26) in which the position of the groove bottom end Eb with respect to the longitudinal axis C served as the reference position corresponds to the first sectional shape. That is, the second sectional area S2 of the second sectional shape is a sectional area which has decreased by the decrease area S'4 from the sectional area of the virtual shape. In the first sectional shape, the groove bottom end Eb (the first bottom end position e1) is located a first bottom end dimension d1 apart from the longitudinal axis C toward the first perpendicular direction. In the second sectional shape, the groove bottom end Eb (the second bottom end position e2) is located a second bottom end dimension d2 larger than the first bottom end dimension d1 apart from the longitudinal axis C in the first perpendicular direction. In the virtual shape, the groove bottom end Eb is located the first bottom end dimension d1 apart from the longitudinal axis C toward the first perpendicular direction.

The first sectional shape is a shape in which the groove portion 32 having the first bottom end dimension d1 and the predetermined groove width dimension b0 is formed in the first columnar shape that has a radius equal to the first diametrical direction dimension R1 and that is point-symmetrical with respect to the longitudinal axis. In the first sectional shape, the first chamfered portions 72A and 72B are formed. The virtual shape and the second sectional shape are shapes in which the groove portion 32 is formed from the second columnar shape that has a radius equal to the second diametrical direction dimension R2 and that is point-symmetrical with respect to the longitudinal axis. In the virtual shape, the groove portion 32 has the first bottom end dimension d1 and the predetermined groove width dimension b0. In the second sectional shape, the groove portion 32 has the second bottom end dimension d2 larger than the first bottom end dimension d1 and the predetermined groove width dimension b0. In the virtual shape and the second sectional shape, the second chamfered portions 75A and 75B having the same shape as the first chamfered portions 72A and 72B are formed. Here, the second columnar shape is a reduced shape analogous to that of the first columnar shape.

If the first sectional shape is compared with the virtual shape, the second diametrical direction dimension R2 of the virtual shape is smaller than the first diametrical direction dimension R1 of the first sectional shape in a diametrical direction dimension between the longitudinal axis C and the outer surface (the first arc-shaped surface 71 and the second arc-shaped surface 73). However, in the first sectional shape and the virtual shape, the position of the groove bottom end Eb of the groove portion 32 with respect to the longitudinal axis C served as the reference position, and the groove width dimension between the groove side surface 77A and the groove side surface 77B are consistent. The shapes of the first chamfered portions 72A and 72B in the first sectional shape and the second chamfered portions 75A and 75B in the virtual shape substantially correspond in the section perpendicular to the longitudinal axis C. The first arc-shaped surface 71 is continuous between the first chamfered portion 72A and the first chamfered portion 72B in the first sectional shape, and the second arc-shaped surface 73 is continuous between the second chamfered portion 75A and the second chamfered portion 75B in the virtual shape. Thus, a virtual gravity center position G'4 which is a gravity center position of the virtual shape is located to the first perpendicular direction side with respect to the gravity center position G of the first sectional shape.

On the other hand, the groove bottom end Eb of the second sectional shape is located to the first perpendicular direction side with respect to those of the first sectional shape and the virtual shape. Thus, the position of the groove bottom end Eb with respect to the longitudinal axis C served as the reference position changes between the first sectional shape and the second sectional shape. The position of the groove bottom end Eb changes so that the gravity center position G in the section perpendicular to the longitudinal axis C in the case where the longitudinal axis C is the reference position is consistent in the first unit component 65 and the second unit component 66.

In the second sectional shape, the groove bottom end Eb is located at the second bottom end position e2 positioned to the first perpendicular direction side with respect to the first bottom end position e1 so that the sectional area is the second sectional area S2 which has decreased by the decrease area S'4 from the sectional area of the virtual shape. That is, in the region located to the first perpendicular direction side with respect to the longitudinal axis C, the sectional area is reduced by the shape change from the virtual shape to the second sectional shape. Thus, the virtual gravity center position G'4 of the virtual shape is located to the first perpendicular direction side with respect to the gravity center position G of the first sectional shape. However, between the first sectional shape and the second sectional shape, the gravity center position G in the case where the longitudinal axis C is the reference position is consistent.

As described above, between the first sectional shape and the second sectional shape, the position of the groove bottom end Eb based on the longitudinal axis C served as the reference position changes so that the gravity center position G in the section perpendicular to the longitudinal axis C in the case where the longitudinal axis C is the reference position is consistent in the first unit component 65 and the second unit component 66. That is, between the first sectional shape and the second sectional shape, the shape of the groove portion 32 in the section perpendicular to the longitudinal axis C changes so that the gravity center position G in the section perpendicular to the longitudinal axis C in the case where the longitudinal axis C is the reference position is consistent in the first unit component 65 and the second unit component 66. Since the gravity center position G in the section perpendicular to the longitudinal axis C in the case where the longitudinal axis C is the reference position is consistent in the first unit component 65 and the second unit component 66, the gravity center position G in the section perpendicular to the longitudinal axis C in the case where the longitudinal axis C is the reference position is consistent over the entire length in the axially parallel directions in the transmission unit 61A.

In each of the other transmission units 61B to 61D as well as in the transmission unit 61A, the gravity center position G in the section perpendicular to the longitudinal axis C in the case where the longitudinal axis C is the reference position is consistent over the entire length in the axially parallel directions. The gravity center position G in the section perpendicular to the longitudinal axis C in the case where the longitudinal axis C is the reference position does not vary between the transmission unit 61A and the transmission unit 61B. Between the transmission unit 61B and the transmission unit 61C and between the transmission unit 61C and the transmission unit 61D as well as between the transmission unit 61A and the transmission unit 61B, the gravity center position G in the section perpendicular to the longitudinal axis C in the case where the longitudinal axis C is the reference position does not change. Therefore, the gravity center position G in the section perpendicular to the longitudinal axis C in the case where the longitudinal axis C is the reference position is consistent over the entire length of the probe body 27 in the axially parallel directions.

In the sectional area changing portion 63 of each of the transmission units 61A to 61D in the ultrasonic probe 3 according to the present embodiment, the gravity center position G with respect to the longitudinal axis C served as the reference position does not vary between the first sectional shape of the first unit component 65 and the second sectional shape of the second unit component 66, as in the first embodiment. That is, in each of the transmission units 61A to 61D, the gravity center position G in the section perpendicular to the longitudinal axis C in the case where the longitudinal axis C is the reference position is consistent over the entire length in the axially parallel directions. Accordingly, even when the sectional area changing portion 63 is provided in each of the transmission units 61A to 61D in which the sectional shape perpendicular to the longitudinal axis C is point-asymmetrical with respect to the longitudinal axis C, the gravity center position G in the section perpendicular to the longitudinal axis C in the case where the longitudinal axis C is the reference position does not change in the sectional area changing portion 63. That is, in the probe body 27, the gravity center position G in the section perpendicular to the longitudinal axis C in the case where the longitudinal axis C is the reference position does not change at positions other than the antinode positions of the ultrasonic vibration. Therefore, the ultrasonic vibration is not affected by the stress even when the sectional area changing portion 63 is provided in each of the transmission units 61A to 61D in which the sectional shape perpendicular to the longitudinal axis C is point-asymmetrical with respect to the longitudinal axis C.

As in the first embodiment, the ultrasonic vibration is not affected by the stress in the ultrasonic probe 3 according to the present embodiment. Therefore, the transmissibility of the ultrasonic vibration is ensured, and the ultrasonic vibration is properly transmitted to the distal face 36 of the ultrasonic probe 3 (the distal side probe member 25). Since the ultrasonic vibration is not easily affected by the stress as in the first embodiment, the strength of the ultrasonic probe 3 is ensured.

In the present embodiment, the position of the groove bottom end Eb of the groove portion 32 differs between the first unit component 65 and the second unit component 66. However, in the formation of each of the transmission units 61A to 61D, the groove portion 32 is first formed by milling so that the groove bottom end Eb is located at the first bottom end position e1 over the entire length in the axially parallel directions. In the second unit component 66 alone, the groove portion 32 is formed so that the groove bottom end Eb is located at the second bottom end position e2. These processes are performed in a short time and at low cost. Thus, each of the transmission units 61A to 61D is efficiently formed at low cost. Therefore, the probe body 27 and the ultrasonic probe 3 can be efficiently manufactured at low cost as in the first embodiment.

Modifications of Third Embodiment

Figure 28:
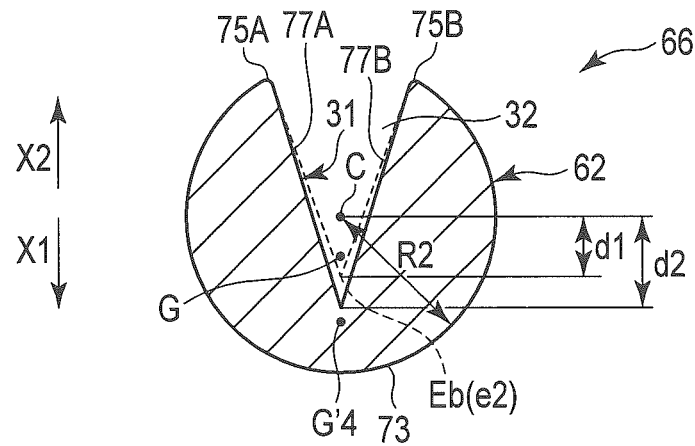
FIG. 28 is a sectional view schematically showing the second unit component of one transmission unit according to the eighth modification in the section perpendicular to the longitudinal axis.

Although the groove defining portion 31 extends in a substantial U-shape in the section perpendicular to the longitudinal axis C in the third embodiment, the groove defining portion 31 is not limited to this form. For example, as in an eighth modification shown in FIG. 27 and FIG. 28, the groove defining portion 31 may extend in a substantial V-shape in the section perpendicular to the longitudinal axis C. In the present modification, the groove bottom surface 78 is not provided, whereas the groove side surfaces 77A and 77B are provided. The groove side surfaces 77A and 77B extend to incline relative to the first perpendicular direction (direction of an arrow X1 in FIG. 27 and FIG. 28) and the second perpendicular direction (direction of an arrow X2 in FIG. 27 and FIG. 28).

In each of the transmission units 61A to 61D according to the present modification as well, the second sectional area S2 of the second sectional shape of the second unit component 66 is smaller than the first sectional area S1 of the first sectional shape of the first unit component 65, as in the third embodiment. In each of the transmission units 61A to 61D, the second diametrical direction dimension R2 from the longitudinal axis C to the second arc-shaped surface 73 in the second sectional shape is smaller than the first diametrical direction dimension R1 from the longitudinal axis C to the first arc-shaped surface 71 in the first sectional shape.

Thus, in the present modification, the virtual gravity center position G'4 of the virtual shape (shape indicated by a dotted line in FIG. 28) is located to the first perpendicular direction side with respect to the gravity center position G of the first sectional shape. Accordingly, in the second sectional shape according to the present modification, the groove bottom end Eb is located at the second bottom end position e2 positioned to the first perpendicular direction side with respect to the first bottom end position e1 of the first sectional shape (virtual shape), as in the third embodiment. As a result, the sectional area perpendicular to the longitudinal axis C has decreased by the decrease area S'4 from the virtual shape. Thus, the virtual gravity center position G'4 of the virtual shape is located to the first perpendicular direction side with respect to the gravity center position G of the first sectional shape. However, between the first sectional shape and the second sectional shape, the gravity center position G in the case where the longitudinal axis C is the reference position is consistent. That is, as in the third embodiment, between the first sectional shape and the second sectional shape, the position of the groove bottom end Eb with respect to the longitudinal axis C served as the reference position changes so that the gravity center position G in the section perpendicular to the longitudinal axis C in the case where the longitudinal axis C is the reference position is consistent in the first unit component 65 and the second unit component 66.

According to the third embodiment and the eighth modification described above, the unit outer surface 62 of each of the transmission units 61A to 61D has only to include the first arc-shaped surface 71 located the first diametrical direction dimension R1 apart from the longitudinal axis C in the first sectional shape, and the second arc-shaped surface 73 located the second diametrical direction dimension R2 smaller than the first diametrical direction dimension R1 apart from the longitudinal axis C in the second sectional shape. Between the first sectional shape and the second sectional shape in each of the transmission units 61A to 61D, the position of the groove bottom end Eb with respect to the longitudinal axis C served as the reference has only to change so that the gravity center position in the section perpendicular to the longitudinal axis C in the case where the longitudinal axis C is the reference position is consistent in the first unit component 65 and the second unit component 66. The second bottom end position e2 of the groove bottom end Eb in the second sectional shape has only to be located to the first perpendicular direction side with respect to the first bottom end position e1 of the groove bottom end Eb in the first sectional shape.

Fourth Embodiment

Figure 29:
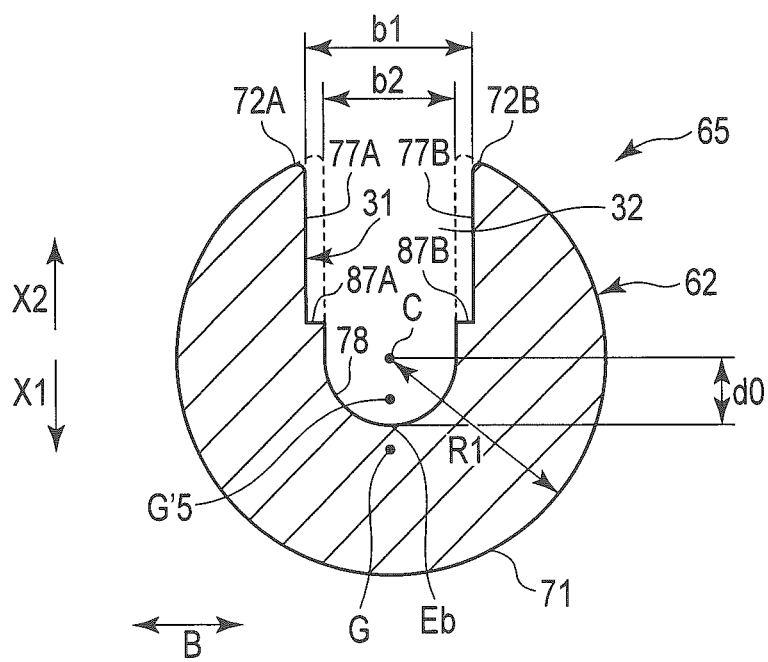
FIG. 29 is a sectional view schematically showing the first unit component of one transmission unit according to a fourth embodiment in the section perpendicular to the longitudinal axis.

Now, a fourth embodiment of the present invention is described with reference to FIG. 29 and FIG. 30. The fourth embodiment is the following modification of the configurations according to the first to third embodiments. The same parts as those according to the first to third embodiments are indicated by the same reference signs, and are not described. Although the transmission unit 61A alone is described below, the other transmission units 61B to 61D are similar to the transmission unit 61A. FIG. 29 shows the section of the first unit component 65 of one transmission unit 61A perpendicular to the longitudinal axis C, and FIG. 20 shows the section of the second unit component 66 of one transmission unit 61A perpendicular to the longitudinal axis C.

Figure 30:
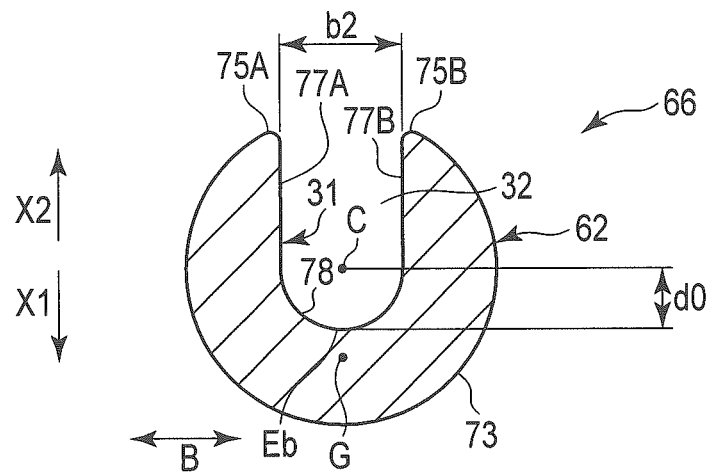
FIG. 30 is a sectional view schematically showing the second unit component of one transmission unit according to the fourth embodiment in the section perpendicular to the longitudinal axis.

As shown in FIG. 29 and FIG. 30, in the present embodiment as well, the second sectional area S2 of the second sectional shape of the second unit component 66 is smaller than the first sectional area S1 of the first sectional shape of the first unit component 65. Therefore, the sectional area of the ultrasonic probe 3 (the probe body 27) perpendicular to the longitudinal axis C decreases in the sectional area changing portion 63. Since the sectional area of the ultrasonic probe 3 perpendicular to the longitudinal axis C decreases at the node position N1 located at a position other than the antinode positions of the ultrasonic vibration, the amplitude of the ultrasonic vibration is increased in the sectional area changing portion 63. As a result, in the present embodiment as well, the ultrasonic vibration increased in amplitude is transmitted to the distal face 36 of the ultrasonic probe 3.

As shown in FIG. 29, the first unit component 65 includes the first arc-shaped surface 71 located the first diametrical direction dimension R1 apart from the longitudinal axis C in the first sectional shape. The first unit component 65 also includes the first chamfered portions 72A and 72B continuous between the first arc-shaped surface 71 and the groove defining portion 31 in the first sectional shape. The first arc-shaped surface 71 is continuous in the directions around the longitudinal axis between the first chamfered portion 72A and the first chamfered portion 72B. Therefore, in the first sectional shape, the first arc-shaped surface 71 is continuous as the outer surface in a part located to the first perpendicular direction side with respect to the longitudinal axis C.

As shown in FIG. 30, the second unit component 66 includes the second arc-shaped surface 73 located the second diametrical direction dimension R2 smaller than the first diametrical direction dimension R1 apart from the longitudinal axis C in the second sectional shape. The second unit component 66 includes the second chamfered portions 75A and 75B continuous between the second arc-shaped surface 73 and the groove defining portion 31 in the second sectional shape. The second arc-shaped surface 73 is continuous in the directions around the longitudinal axis between the second chamfered portion 75A and the second chamfered portion 75B. Therefore, in the second sectional shape, the second arc-shaped surface 73 is continuous as the outer surface in the part located to the first perpendicular direction side with respect to the longitudinal axis C. In the present embodiment as well as in the second embodiment, the shapes of the second chamfered portions 75A and 75B do not change relative to the first chamfered portions 72A and 72B between the first sectional shape and the second sectional shape.

In the transmission unit 61A (61B to 61D), as in the first embodiment, the position of the groove bottom surface 78 with respect to the longitudinal axis C served as the reference position in the section perpendicular to the longitudinal axis C is consistent over the entire length in the axially parallel directions. Thus, in the transmission unit 61A (61B to 61D), the position of the groove bottom end Eb based on the longitudinal axis C served as the reference position in the first perpendicular direction and the second perpendicular direction in the section perpendicular to the longitudinal axis C is consistent over the entire length in the axially parallel directions. That is, the position of the groove bottom end Eb with respect to the longitudinal axis C served as the reference position does not vary between the first sectional shape of the first unit component 65 and the second sectional shape of the second unit component 66.

However, in the transmission unit 61A (61B to 61D) according to the present embodiment, in contrast with the first embodiment and the second embodiment, the positions of the groove side surfaces 77A and 77B with respect to the longitudinal axis served as the reference differs between the first sectional shape and the second sectional shape. Thus, in the transmission unit 61A (61B to 61D), the groove width dimension in the groove width directions between the groove side surface 77A and the groove side surface 77B differs between the first sectional shape and the second sectional shape. In the first sectional shape, the groove portion 32 has a first groove width dimension b1 in a part located to the second perpendicular direction side of the longitudinal axis C. In the second sectional shape, the groove portion 32 has a second groove width dimension b2 smaller than the first groove width dimension b1 in the part located to the second perpendicular direction side of the longitudinal axis C. That is, the groove defining portion 31 includes groove width increase surfaces 87A and 87B which increase the groove width dimension of the groove portion 32 in the region of the first sectional shape located to the second perpendicular direction side with respect to the longitudinal axis C.

In the first sectional shape, the groove width dimension of the groove portion 32 increases in the region located to the second perpendicular side with respect to the longitudinal axis C so that the sectional area perpendicular to the longitudinal axis C decreases by a decrease area S'5 from the virtual shape (shape indicated by a dotted line in FIG. 29) in which the groove width dimension of the groove portion 32 in the region located to the second perpendicular side with respect to the longitudinal axis C corresponds to that of the second sectional shape (the second groove width dimension b2). That is, the first sectional area S1 of the first sectional shape is a sectional area which has decreased by the decrease area S'5 from the sectional area of the virtual shape.

The first sectional shape and the virtual shape are shapes in which the groove portion 32 is formed in the first columnar shape that has a radius equal to the first diametrical direction dimension R1 and that is point-symmetrical with respect to the longitudinal axis. In the first sectional shape, the groove portion 32 has the predetermined bottom end dimension d0 and the first groove width dimension b1. In the virtual shape, the groove portion 32 has the predetermined bottom end dimension d0 and the second groove width dimension b2 smaller than the first groove width dimension b1. In the first sectional shape and the virtual shape, the first chamfered portions 72A and 72B are formed. In the second sectional shape, the groove portion 32 having the predetermined bottom end dimension d0 and the second groove width dimension b2 is formed from the second columnar shape which has a radius equal to the second diametrical direction dimension R2 and which is point-symmetrical with respect to the longitudinal axis. In the second sectional shape, the second chamfered portions 75A and 75B having the same shape as the first chamfered portions 72A and 72B are formed. Here, the second columnar shape is a reduced shape analogous to that of the first columnar shape.

If the virtual shape is compared with the second sectional shape, the second diametrical direction dimension R2 of the second sectional shape is smaller than the first diametrical direction dimension R1 of the virtual shape in a diametrical direction dimension between the longitudinal axis C and the outer surface (the first arc-shaped surface 71 and the second arc-shaped surface 73). However, in the virtual shape and the second sectional shape, the position of the groove bottom end Eb of the groove portion 32 with respect to the longitudinal axis C served as the reference position, and the groove width dimension (the second groove width dimension b2) between the groove side surface 77A and the groove side surface 77B are consistent. The shapes of the first chamfered portions 72A and 72B in the virtual shape and the second chamfered portions 75A and 75B in the second sectional shape substantially correspond in the section perpendicular to the longitudinal axis. The first arc-shaped surface 71 is continuous between the first chamfered portion 72A and the first chamfered portion 72B in the virtual shape, and the second arc-shaped surface 73 is continuous between the second chamfered portion 75A and the second chamfered portion 75B in the second sectional shape. Thus, a virtual gravity center position G'5 which is a gravity center position of the virtual shape is located to the second perpendicular direction side with respect to the gravity center position G of the second sectional shape.

On the other hand, in the region located to the second perpendicular side of the longitudinal axis C, the groove width dimension is larger in the first sectional shape than in the second sectional shape and the virtual shape. Thus, the groove width dimension of the groove portion 32 in the groove width directions changes between the first sectional shape and the second sectional shape. The groove width dimension changes so that the gravity center position G in the section perpendicular to the longitudinal axis C in the case where the longitudinal axis C is the reference position is consistent in the first unit component 65 and the second unit component 66.

In the first sectional shape, the groove width dimension is the first groove width dimension b1 larger than the second groove width dimension b2 in the region located to the second perpendicular side of the longitudinal axis C so that the sectional area is the first sectional area S1 which has decreased by the decrease area S'5 from the sectional area of the virtual shape. That is, in the region located to the second perpendicular direction side with respect to the longitudinal axis C, the sectional area is reduced by the shape change from the virtual shape to the first sectional shape. Thus, the virtual gravity center position G'5 of the virtual shape is located to the second perpendicular direction side with respect to the gravity center position G of the second sectional shape. However, between the first sectional shape and the second sectional shape, the gravity center position G in the case where the longitudinal axis C is the reference position is consistent.

As described above, between the first sectional shape and the second sectional shape, the groove width dimension of the groove portion 32 in the groove width directions changes so that the gravity center position G in the section perpendicular to the longitudinal axis C in the case where the longitudinal axis C is the reference position is consistent in the first unit component 65 and the second unit component 66. That is, between the first sectional shape and the second sectional shape, the shape of the groove portion 32 in the section perpendicular to the longitudinal axis C changes so that the gravity center position G in the section perpendicular to the longitudinal axis C in the case where the longitudinal axis C is the reference position is consistent in the first unit component 65 and the second unit component 66. Since the gravity center position G in the section perpendicular to the longitudinal axis C in the case where the longitudinal axis C is the reference position is consistent in the first unit component 65 and the second unit component 66, the gravity center position G in the section perpendicular to the longitudinal axis C in the case where the longitudinal axis C is the reference position is consistent over the entire length in the axially parallel directions in the transmission unit 61A.

In each of the other transmission units 61B to 61D as well as in the transmission unit 61A, the gravity center position G in the section perpendicular to the longitudinal axis C in the case where the longitudinal axis C is the reference position is consistent over the entire length in the axially parallel directions. The gravity center position G in the section perpendicular to the longitudinal axis C in the case where the longitudinal axis C is the reference position does not vary between the transmission unit 61A and the transmission unit 61B. Between the transmission unit 61B and the transmission unit 61C and between the transmission unit 61C and the transmission unit 61D as well as between the transmission unit 61A and the transmission unit 61B, the gravity center position G in the section perpendicular to the longitudinal axis C in the case where the longitudinal axis C is the reference position does not change. Therefore, the gravity center position G in the section perpendicular to the longitudinal axis C in the case where the longitudinal axis C is the reference position is consistent over the entire length of the probe body 27 in the axially parallel directions.

In the sectional area changing portion 63 of each of the transmission units 61A to 61D in the ultrasonic probe 3 according to the present embodiment, the gravity center position G with respect to the longitudinal axis C served as the reference position does not vary between the first sectional shape of the first unit component 65 and the second sectional shape of the second unit component 66, as in the first embodiment. That is, in each of the transmission units 61A to 61D, the gravity center position G in the section perpendicular to the longitudinal axis C in the case where the longitudinal axis C is the reference position is consistent over the entire length in the axially parallel directions. Accordingly, even when the sectional area changing portion 63 is provided in each of the transmission units 61A to 61D in which the sectional shape perpendicular to the longitudinal axis C is point-asymmetrical with respect to the longitudinal axis C, the gravity center position G in the section perpendicular to the longitudinal axis C in the case where the longitudinal axis C is the reference position does not change in the sectional area changing portion 63. That is, in the probe body 27, the gravity center position G in the section perpendicular to the longitudinal axis C in the case where the longitudinal axis C is the reference position does not change at positions other than the antinode positions of the ultrasonic vibration. Therefore, the ultrasonic vibration is not affected by the stress even when the sectional area changing portion 63 is provided in each of the transmission units 61A to 61D in which the sectional shape perpendicular to the longitudinal axis C is point-asymmetrical with respect to the longitudinal axis C.

As in the first embodiment, the ultrasonic vibration is not affected by the stress in the ultrasonic probe 3 according to the present embodiment. Therefore, the transmissibility of the ultrasonic vibration is ensured, and the ultrasonic vibration is properly transmitted to the distal face 36 of the ultrasonic probe 3 (the distal side probe member 25). Since the ultrasonic vibration is not easily affected by the stress as in the first embodiment, the strength of the ultrasonic probe 3 is ensured.

In the present embodiment, the groove width dimension of the groove portion 32 differs between the first unit component 65 and the second unit component 66. However, in the formation of each of the transmission units 61A to 61D, the groove portion 32 is first formed by milling so that the groove width dimension is the second groove width dimension b2 over the entire length in the axially parallel directions. In the first unit component 65 alone, the groove portion 32 is formed so that the groove width dimension is the first groove width dimension b1. These processes are performed in a short time and at low cost. Thus, each of the transmission units 61A to 61D is efficiently formed at low cost. Therefore, the probe body 27 and the ultrasonic probe 3 can be efficiently manufactured at low cost as in the first embodiment.

Modifications of Fourth Embodiment

Figure 31:
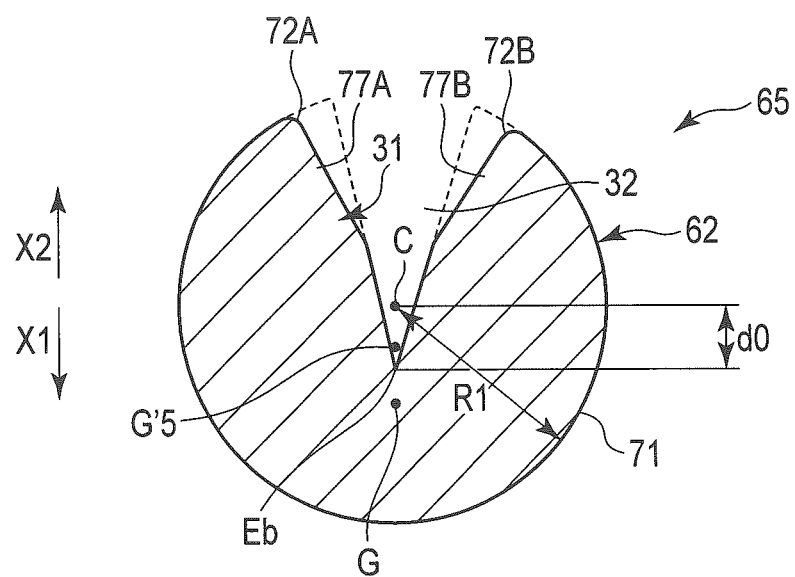
FIG. 31 is a sectional view schematically showing the first unit component of one transmission unit according to a ninth modification in the section perpendicular to the longitudinal axis.

Although the groove defining portion 31 includes the groove bottom surface 78 in the fourth embodiment, the groove defining portion 31 is not limited to this form. For example, as in a ninth modification shown in FIG. 31 and FIG. 32, no groove bottom surface 78 may be provided, and a vertex position formed by the groove side surface 77A and the groove side surface 77B may be the groove bottom end Eb. The groove side surfaces 77A and 77B extend to incline relative to the first perpendicular direction (direction of an arrow X1 in FIG. 31 and FIG. 32) and the second perpendicular direction (direction of an arrow X2 in FIG. 31 and FIG. 32).

In each of the transmission units 61A to 61D according to the present modification as well, the second sectional area S2 of the second sectional shape of the second unit component 66 is smaller than the first sectional area S1 of the first sectional shape of the first unit component 65, as in the fourth embodiment. In each of the transmission units 61A to 61D, the second diametrical direction dimension R2 from the longitudinal axis C to the second arc-shaped surface 73 in the second sectional shape is smaller than the first diametrical direction dimension R1 from the longitudinal axis C to the first arc-shaped surface 71 in the first sectional shape.

Thus, in the present modification, the virtual gravity center position G'5 of the virtual shape (shape indicated by a dotted line in FIG. 31) is located to the second perpendicular direction side with respect to the gravity center position G of the second sectional shape. Accordingly, in the first sectional shape according to the present modification, the groove width dimension is larger than the groove width dimension of the virtual shape in the region located to the second perpendicular direction side of the longitudinal axis C, as in the fourth embodiment. As a result, the sectional area perpendicular to the longitudinal axis C has decreased by the decrease area S'5 from the virtual shape. Thus, the virtual gravity center position G'5 of the virtual shape is located to the second perpendicular direction side with respect to the gravity center position G of the second sectional shape. However, between the first sectional shape and the second sectional shape, the gravity center position G in the case where the longitudinal axis C is the reference position is consistent. That is, as in the fourth embodiment, between the first sectional shape and the second sectional shape, the groove width dimension of the groove portion 32 changes in a part located to the second perpendicular direction side with respect to the longitudinal axis C so that the gravity center position G in the section perpendicular to the longitudinal axis C in the case where the longitudinal axis C is the reference position is consistent in the first unit component 65 and the second unit component 66.

According to the fourth embodiment and the ninth modification described above, the unit outer surface 62 of each of the transmission units 61A to 61D has only to include the first arc-shaped surface 71 located the first diametrical direction dimension R1 apart from the longitudinal axis C in the first sectional shape, and the second arc-shaped surface 73 located the second diametrical direction dimension R2 smaller than the first diametrical direction dimension R1 apart from the longitudinal axis C in the second sectional shape. Between the first sectional shape and the second sectional shape of each of the transmission units 61A to 61D, the groove width dimension of the groove portion 32 in the groove width directions has only to change so that the gravity center position G in the section perpendicular to the longitudinal axis C in the case where the longitudinal axis C is the reference position is consistent in the first unit component 65 and the second unit component 66. The second groove width dimension (b2) in the second sectional shape has only to be smaller than the first groove width dimension (b1) in the first sectional shape in the part located to the second perpendicular direction side with respect to the longitudinal axis C.

Configuration Associated with Third Embodiment and Fourth Embodiment

In the third embodiment, the position of the groove bottom end Eb with respect to the longitudinal axis C served as the reference changes between the first sectional shape and the second sectional shape. In the fourth embodiment, the groove width dimension of the groove portion 32 changes between the first sectional shape and the second sectional shape. In the third embodiment, the shape of the groove portion 32 in the section perpendicular to the longitudinal axis C changes in accordance with the change of the position of the groove bottom end Eb. In the fourth embodiment, the shape of the groove portion 32 in the section perpendicular to the longitudinal axis C changes in accordance with the change of the groove width dimension.

Therefore, in the ultrasonic probe 3 having the configuration associated with the third embodiment and the fourth embodiment (the eighth modification and the ninth modification are included), the unit outer surface 62 of each of the transmission units 61A to 61D includes the first arc-shaped surface 71 located the first diametrical direction dimension R1 apart from the longitudinal axis C in the first sectional shape, and the second arc-shaped surface 73 located the second diametrical direction dimension R2 smaller than the first diametrical direction dimension R1 apart from the longitudinal axis C in the second sectional shape. Between the first sectional shape and the second sectional shape, the shape of the groove portion 32 in the section perpendicular to the longitudinal axis C changes so that the gravity center position G in the section perpendicular to the longitudinal axis C in the case where the longitudinal axis C is the reference position is consistent in the first unit component 65 and the second unit component 66.

Other Modifications

Figure 35:
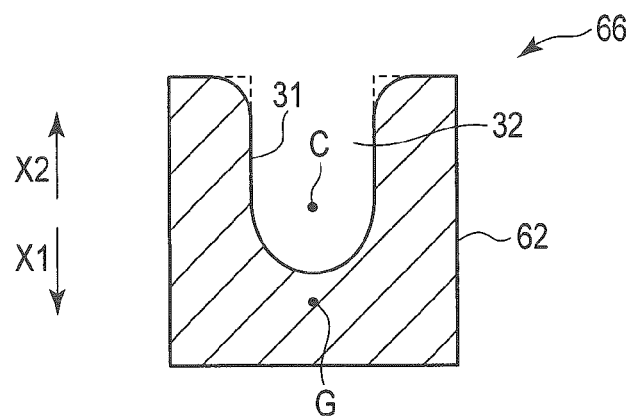
FIG. 35 is a sectional view taken along the line 35-35 of FIG. 33.

In the embodiments and the modifications described above, the first sectional shape has the first arc-shaped surface 71, and the second sectional shape has the second arc-shaped surface 73. However, the present invention is not limited to this. For example, as in a tenth modification shown in FIG. 33 to FIG. 35, no arc-shaped surface around the longitudinal axis C may be provided on the unit outer surface 62 of each of the transmission units 61A to 61D. In the present modification, the first sectional shape is a shape in which the groove portion 32 is formed from the quadrate first columnar shape that is point-symmetrical with respect to the longitudinal axis C. The second sectional shape is a shape in which the groove portion 32 is formed in the second columnar shape that is a quadrate point-symmetrical with respect to the longitudinal axis C and that is a reduced shape analogous to that of the first columnar shape. In the present modification as well as in the embodiments described above, the groove portion 32 is formed over the entire length in the axially parallel directions in each of the transmission units 61A to 61D. The groove portion 32 is depressed from the unit outer surface 62 toward the first perpendicular direction (direction of an arrow X1 in FIG. 34 and FIG. 35) perpendicular to the longitudinal axis C, and is open toward the second perpendicular direction (direction of an arrow X2 in FIG. 34 and FIG. 35) opposite to the first perpendicular direction.

In the present modification as well, the proximal end and the distal end of each of the transmission units 61A to 61D are the antinode positions of the ultrasonic vibration. For example, in the transmission unit 61A, the proximal end is the antinode position (first antinode position) A1, and the distal end is the antinode position (second antinode position) A2. Each of the transmission units 61A to 61D is provided with the sectional area changing portion 63 which changes the sectional area perpendicular to the longitudinal axis C. The sectional area changing portion 63 is provided so that the second sectional area S2 of the second sectional shape of the second unit component 66 is smaller than the first sectional area S1 of the first sectional shape of the first unit component 65. In each of the transmission units 61A to 61D, the sectional area changing portion 63 is located at the node position which is a position other than the antinode positions of the ultrasonic vibration, so that the amplitude of the ultrasonic vibration is increased. For example, in the transmission unit 61A, the sectional area changing portion 63 is located at the node position N1 between the antinode position A1 and the antinode position A2.

In the present modification as well as in the embodiments described above, the shape changes between the first sectional shape and the second sectional shape so that the gravity center position G in the section perpendicular to the longitudinal axis C in the case where the longitudinal axis C is the reference position is consistent in the first unit component 65 and the second unit component 66. That is, in each of the transmission units 61A to 61D, the gravity center position G in the section perpendicular to the longitudinal axis C in the case where the longitudinal axis C is the reference position is consistent over the entire length in the axially parallel directions. Therefore, the ultrasonic vibration is not affected by the stress even when the sectional area changing portion 63 is provided in each of the transmission units 61A to 61D in which the sectional shape perpendicular to the longitudinal axis C is point-asymmetrical with respect to the longitudinal axis C.

Figure 36:
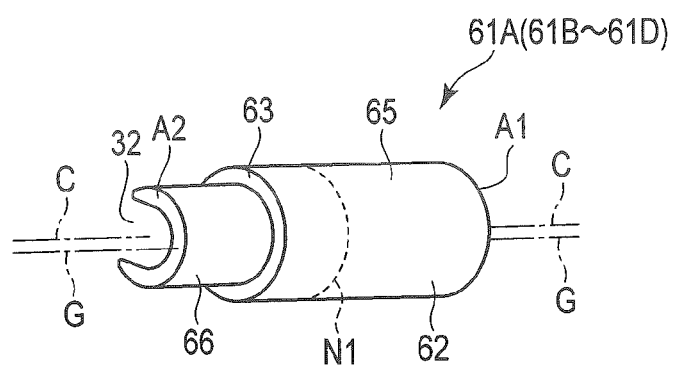
FIG. 36 is a perspective view schematically showing the configuration of one transmission unit of a probe body according to an eleventh modification.

In the embodiments and the modifications described above, the sectional area changing portion 63 is located at the node position of the ultrasonic vibration in each of the transmission units 61A to 61D. However, the present invention is not limited to this. For example, as in an eleventh modification shown in FIG. 36, the sectional area changing portion 63 may be located at a position different from the node position (N1) of the ultrasonic vibration in one transmission unit 61A. However, in the present modification as well as in the embodiments described above, the sectional area changing portion 63 is located at the position other than the antinode positions (e.g., A1 and A2) of the ultrasonic vibration. The sectional area changing portion 63 is located at the position other than the antinode positions of the ultrasonic vibration so that the amplitude of the ultrasonic vibration is increased in the sectional area changing portion 63. Here, when the position of the sectional area changing portion 63 is closer to the node position, the increase ratio of the amplitude of the ultrasonic vibration is higher. When the sectional area changing portion 63 is located at the node position, the increase rate of the amplitude of the ultrasonic vibration is highest.

Figure 37:
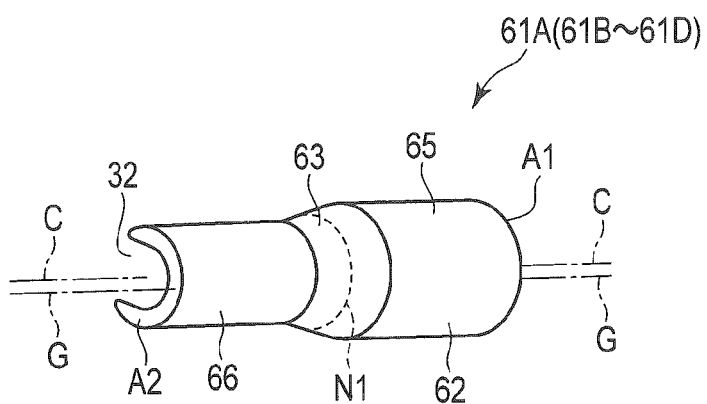
FIG. 37 is a perspective view schematically showing the configuration of one transmission unit of a probe body according to a twelfth modification.

In the embodiments and the modifications described above, the sectional area changing portion 63 is stepped in each of the transmission units 61A to 61D. However, the present invention is not limited to this. For example, as in a twelfth modification shown in FIG. 37, the sectional area changing portion 63 may be tapered in one transmission unit 61A. In the sectional area changing portion according to the present modification, the sectional area perpendicular to the longitudinal axis C decreases from the proximal direction toward the distal direction. In the present modification as well as in the embodiments described above, the sectional area changing portion 63 is located at the position other than the antinode positions (e.g., A1 and A2) of the ultrasonic vibration. The sectional area changing portion 63 is located at the position other than the antinode positions of the ultrasonic vibration so that the amplitude of the ultrasonic vibration is increased in the sectional area changing portion 63.

In the embodiments and the modifications described above, in the ultrasonic probe 3, the distal end of the cylindrical distal side probe member 25 is the distal end of the ultrasonic probe 3. However, the present invention is not limited to this. For example, as in a thirteenth modification shown in FIG. 38, the distal end of the probe body 27 may be the distal end of the ultrasonic probe 3. In the present modification, the probe body 27 is provided in a probe member 89. In the probe member 89, a cylindrical connection portion 91 is continuous with the proximal direction side of the probe body 27. The probe member 89 is connected to the distal direction side of the horn member 12 by the connection portion 91.

Although four transmission units 61A to 61D are provided in the probe body 27 in the embodiments and the modifications described above, the present invention is not limited to this. One transmission unit (61A to 61D) need only be provided in the probe body 27.

A jaw (not shown) configured to open and close relative to the distal portion of the ultrasonic probe 3 may be provided in the distal portion of the sheath 4. When the jaw is provided, a living tissue can be treated while the living tissue is grasped between the distal portion of the ultrasonic probe 3 and the jaw. For example, the living tissue is ultrasonically coagulated and cut by the ultrasonic vibration while the living tissue is grasped between the distal portion of the ultrasonic probe 3 and the jaw. A bipolar treatment is also conducted by a high-frequency current using the distal portion of the ultrasonic probe 3 and the jaw as electrodes.

According to the embodiments and the modifications described above, the ultrasonic probe 3 has only to include the transmission unit (61A to 61D) in which the sectional shape perpendicular to the longitudinal axis C is point-asymmetrical with respect to the longitudinal axis C. In the section of the transmission unit (61A to 61D) perpendicular to the longitudinal axis C, the groove portion 32 which is depressed from the unit outer surface 62 toward the first perpendicular direction perpendicular to the longitudinal axis and which is open with respect to the outside toward the second perpendicular direction opposite to the first perpendicular direction has only to be defined. The groove portion 32 has only to be defined over the entire length of the transmission unit (61A to 61D) in the axially parallel directions parallel to the longitudinal axis C. The sectional area changing portion 63 which changes the sectional area perpendicular to the longitudinal axis C has only to be provided in the transmission unit (61A to 61D) in which the groove portion 32 is provided. In the transmission unit (61A to 61D), the gravity center position G in the section perpendicular to the longitudinal axis C in the case where the longitudinal axis C is the reference position has only to be consistent over the entire length in the axially parallel directions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe that has a longitudinal axis and that extends along the longitudinal axis from a proximal side toward a distal side, the ultrasonic probe being configured to transmit an ultrasonic vibration, the ultrasonic probe comprising:

a first unit component that includes:
  a first outer peripheral surface extending along the longitudinal axis, the first outer peripheral surface has a constant outer diameter throughout the entire length of the first unit component in a longitudinal direction,
  a first groove being depressed from the first outer peripheral surface toward the longitudinal axis,
  a first sectional area, and
  a first center of gravity in a section perpendicular to the longitudinal axis, a position of the first center of gravity being defined in accordance with a depth of the first groove from the first outer peripheral surface;
a second unit component that includes:
  a second outer peripheral surface extending along the longitudinal axis, the second outer peripheral surface has a constant outer diameter throughout the entire length of the second unit component in the longitudinal direction, and the outer diameter of the first unit component is different from the outer diameter of the second unit component,
  a second groove being depressed from the second outer peripheral surface toward the longitudinal axis,
  a second sectional area,
    the second sectional area in the second unit component being smaller than the first sectional area in the first unit component, and
  a second center of gravity in the section perpendicular to the longitudinal axis, a position of the second center of gravity being defined in accordance with a depth of the second groove from the second outer peripheral surface, the position of the second center of gravity relative to the longitudinal axis coinciding with the position of the first center of gravity relative to the longitudinal axis; and
a sectional area decreasing portion in which the first unit component and the second unit component are fixedly connected to each other,
  the sectional area decreasing portion including a sectional area that is perpendicular to the longitudinal axis and that decreases from the first unit component toward the second unit component so that the position of the second center of gravity relative to the longitudinal axis coincides with the position of the first center of gravity relative to the longitudinal axis, and so that a bottom position of the second groove relative to the longitudinal axis in the section perpendicular to the longitudinal axis in the second unit component coincides with a bottom position of the first groove relative to the longitudinal axis in the section perpendicular to the longitudinal axis in the first unit component wherein a gravitational-center axis that passes through the first center of gravity and the second center of gravity is located on an opposite side of openings of the first groove and the second groove with respect to the longitudinal axis, and the gravitational-center axis is parallel to the longitudinal axis.

2. The ultrasonic probe according to claim 1, wherein the ultrasonic probe is configured to:
transmit the ultrasonic vibration so that the ultrasonic probe vibrates in a predetermined vibrating state;
vibrate in the predetermined vibrating state so that a vibration node is located in the sectional area decreasing portion; and increase an amplitude of the ultrasonic vibration in the sectional area decreasing portion in the predetermined vibration state.

3. The ultrasonic probe according to claim 1, wherein
the bottom position of the first groove relative to the longitudinal axis in the section perpendicular to the longitudinal axis is consistent over the entire length of the first unit component in the longitudinal direction;
the bottom position of the second groove relative to the longitudinal axis in the section perpendicular to the longitudinal axis is consistent over the entire length of the second unit component in the direction along the longitudinal axis; and
a shape of the first outer peripheral surface in the section perpendicular to the longitudinal axis is changed into a shape of the second outer peripheral surface in the section perpendicular to the longitudinal axis in the sectional area decreasing portion between the first unit component and the second unit component, so that the position of the first center of gravity relative to the longitudinal axis in the first unit component coincides with the position of the second center of gravity relative to the longitudinal axis in the second unit component.

4. The ultrasonic probe according to claim 1, wherein a shape of the first groove in the section perpendicular to the longitudinal axis is changed into a shape of the second groove in the section perpendicular to the longitudinal axis in the sectional area decreasing portion between the first unit component and the second unit component so that the position of the first center of gravity relative to the longitudinal axis in the first unit component coincides with the position of the second center of gravity relative to the longitudinal axis in the second unit component.

5. The ultrasonic probe according to claim 1, wherein when a first perpendicular direction and a second perpendicular direction, opposite to the first peripheral direction, are each perpendicular to the longitudinal axis, and a reference axis, which extends along the first perpendicular direction and the second perpendicular direction and which passes through the longitudinal axis, is defined in the section perpendicular to the longitudinal axis, the first center of gravity is located on the reference axis in the section perpendicular to the longitudinal axis in the first unit component, and the second center of gravity is located on the reference axis in the section perpendicular to the longitudinal axis in the second unit component.

6. The ultrasonic probe according to claim 1, wherein when a first perpendicular direction and a second perpendicular direction, opposite to the first peripheral direction, are each perpendicular to the longitudinal axis, each of the first groove and the second groove is depressed toward the first perpendicular direction; and
the bottom position of the first groove is located on a first perpendicular direction side with respect to the longitudinal axis over the entire length of the first unit component in the direction along the longitudinal axis, and the bottom position of the second groove is located on the first perpendicular direction side with respect to the longitudinal axis over the entire length of the second unit component in the direction along the longitudinal axis.

7. The ultrasonic probe according to claim 1, wherein the ultrasonic probe is configured to:
transmit the ultrasonic vibration so that the ultrasonic probe vibrates in a predetermined vibrating state; and
vibrate in the predetermined vibrating state so that any vibration anti-nodes are spaced from the sectional area decreasing portion in the direction along the longitudinal axis.

8. The ultrasonic probe according to claim 1, wherein a length of the sectional area decreasing portion is smaller than a length of the first unit component in a direction along the longitudinal axis and is smaller than a length of the second unit component in the direction along the longitudinal axis.

9. The ultrasonic probe according to claim 1, further comprising a tube member that extends through an inside of the first groove and an inside of the second grove along the longitudinal axis.

10. The ultrasonic probe according to claim 1, wherein:
the first unit component is one of a plurality of first unit components;
the second unit component is one of a plurality of second unit components; and
the first unit components and the second unit components are alternately arranged in the longitudinal direction.

11. An ultrasonic probe that has a longitudinal axis and that extends along the longitudinal axis from a proximal side toward a distal side, the ultrasonic probe being configured to transmit an ultrasonic vibration, the ultrasonic probe comprising:
a first unit component that includes:
a first outer peripheral surface extending along the longitudinal axis, the first outer peripheral surface has a constant outer diameter throughout the entire length of the first unit component in a longitudinal direction,
a first groove being depressed from the first outer peripheral surface toward the longitudinal axis,
a first sectional area, and
a first center of gravity in a section perpendicular to the longitudinal axis, a position of the first center of gravity being defined in accordance with a depth of the first groove from the first outer peripheral surface;
a second unit component that includes:
a second outer peripheral surface extending along the longitudinal axis, the second outer peripheral surface has a constant outer diameter throughout the entire length of the second unit component in the longitudinal direction, and the outer diameter of the first unit component is different from the outer diameter of the second unit component,
a second groove being depressed from the second outer peripheral surface toward the longitudinal axis,
a second sectional area,
the second sectional area in the second unit component being smaller than the first sectional area in the first unit component, and
a second center of gravity in the section perpendicular to the longitudinal axis, a position of the second center of gravity being defined in accordance with a depth of the second groove from the second outer peripheral surface, the position of the second center of gravity relative to the longitudinal axis coinciding with the position of the first center of gravity relative to the longitudinal axis; and
a sectional area decreasing portion in which the first unit component and the second unit component are fixedly connected to each other, the sectional area decreasing portion including a sectional area that is perpendicular to the longitudinal axis and that decreases from the first unit component toward the second unit component so that the position of the second center of gravity relative to the longitudinal axis coincides with the position of the first center of gravity relative to the longitudinal axis, and so that a position of a groove side surface of the second groove relative to the longitudinal axis in the section perpendicular to the longitudinal axis in the second unit component coincides with a position of a groove side surface of the first groove in the section perpendicular to the longitudinal axis in the first unit component, wherein a gravitational-center axis that passes through the first center of gravity and the second center of gravity is located on an opposite side of openings of the first groove and the second groove with respect to the longitudinal axis, and the gravitational-center axis is parallel to the longitudinal axis.

12. The ultrasonic probe according to claim 11, wherein a length of the sectional area decreasing portion is smaller than a length of the first unit component in a direction along the longitudinal axis and is smaller than a length of the second unit component in the direction along the longitudinal axis.

13. The ultrasonic probe according to claim 11, further comprising a tube member that extends through an inside of the first groove and an inside of the second grove along the longitudinal axis.

14. The ultrasonic probe according to claim 11, wherein:
the first unit component is one of a plurality of first unit components;
the second unit component is one of a plurality of second unit components; and
the first unit components and the second unit components are alternately arranged in the longitudinal direction.

* * * * *